(12) United States Patent
Gillette et al.

(10) Patent No.: US 12,681,003 B2
(45) Date of Patent: Jul. 14, 2026

(54) METHODS AND DEVICES FOR MONITORING MACHINE FLUIDS

(71) Applicant: LogiLube, LLC, Loveland, CO (US)

(72) Inventors: William J. Gillette, Loveland, CO (US); Keith Dirks, Loveland, CO (US)

(73) Assignee: LogiLube, LLC, Loveland, CO (US)

( * ) Notice: Subject to any disclaimer, the term of this patent is extended or adjusted under 35 U.S.C. 154(b) by 159 days.

(21) Appl. No.: 18/455,452

(22) Filed: Aug. 24, 2023

(65) Prior Publication Data

US 2023/0400448 A1 Dec. 14, 2023

Related U.S. Application Data

(63) Continuation of application No. 17/160,366, filed on Jan. 27, 2021, now Pat. No. 11,761,946.

(Continued)

(51) Int. Cl.
| | |
|---|---|
| *G01N 33/30* | (2006.01) |
| *G01N 33/28* | (2006.01) |
| *H04Q 9/00* | (2006.01) |

(52) U.S. Cl.
CPC ......... *G01N 33/30* (2013.01); *G01N 33/2847* (2013.01); *G01N 33/2858* (2013.01); *G01N 33/2876* (2013.01); *H04Q 9/00* (2013.01)

(58) Field of Classification Search
CPC ............... G01N 33/30; G01N 33/2847; G01N 33/2858; G01N 33/2876; G01N 33/2888; G01N 1/2035; G01N 11/08; H04Q 9/00;

F01M 11/10; F01M 2011/14; F16N 29/04; F16N 2200/04; F16N 2200/12; F16N 2200/20; F16N 2250/50; G08B 5/36; G08B 23/00
See application file for complete search history.

(56) References Cited

U.S. PATENT DOCUMENTS

| | | | |
|---|---|---|---|
| 2,550,420 A | 4/1951 | McNatt | |
| 4,150,578 A | 4/1979 | Swartz | |
| | (Continued) | | |

FOREIGN PATENT DOCUMENTS

| | | |
|---|---|---|
| CN | 203287110 | 11/2013 |
| CN | 204575589 | 8/2015 |
| | (Continued) | |

OTHER PUBLICATIONS

TE Sensor Solutions, 'FPS2800B12C4 Fluid Property Sensor Datasheet', Sep. 1, 2015, Viewed on and retrieved from the Internet on Aug. 24, 2023, <URL: https://www.te.com/usa-en/product-FPP800A110. datasheet.pdf.

*Primary Examiner* — Alvaro E Fortich
*Assistant Examiner* — Carl F.R. Tchatchouang
(74) *Attorney, Agent, or Firm* — SNELL & WILMER L.L.P.

(57) ABSTRACT

A device for measuring fluid parameters may be modular or integrally formed. The device is positioned on a machine that includes one or more fluids to be monitored, and the device includes a (1) controller, (2) spacer that connects to a power source and that may include one or more connectors to connect to remote sensors, and (3) an optional manifold through which the fluid may pass. The manifold could include fluid sensors and/or be connectable to a sample bottle for the purpose of taking fluid samples.

15 Claims, 27 Drawing Sheets

Related U.S. Application Data

(60) Provisional application No. 62/966,484, filed on Jan. 27, 2020.

(56) References Cited

U.S. PATENT DOCUMENTS

| | | | |
|---|---|---|---|
| 4,405,829 A | 9/1983 | Rivest et al. | |
| 4,428,344 A | 1/1984 | Focht | |
| 4,539,643 A | 9/1985 | Suzuki et al. | |
| 4,715,451 A | 12/1987 | Bseisu et al. | |
| 5,213,477 A | 5/1993 | Watanabe et al. | |
| 5,303,842 A | 4/1994 | Harp et al. | |
| 5,347,859 A | 9/1994 | Henneuse et al. | |
| 5,383,241 A | 1/1995 | Krieger | |
| 5,552,791 A | 9/1996 | Metal | |
| 5,560,179 A | 10/1996 | Leifeld | |
| 5,587,055 A | 12/1996 | Hartman et al. | |
| 5,748,075 A | 5/1998 | Dirmeyer et al. | |
| 5,928,492 A | 7/1999 | Corlett et al. | |
| 5,988,206 A | 11/1999 | Bare et al. | |
| 6,021,377 A | 2/2000 | Dubinsky et al. | |
| 6,170,318 B1 | 1/2001 | Lewis | |
| 6,357,493 B1 | 3/2002 | Shermer et al. | |
| 6,644,360 B1 | 11/2003 | Sobata et al. | |
| 6,747,572 B2 | 6/2004 | Bocko et al. | |
| 6,810,718 B2 * | 11/2004 | Wilson | G01N 23/223 |
| | | | 702/108 |
| 7,292,143 B2 | 11/2007 | Drake et al. | |
| 7,521,138 B2 | 4/2009 | Pearson | |
| 7,596,461 B2 | 9/2009 | Hart et al. | |
| 8,147,302 B2 | 4/2012 | Desrochers et al. | |
| 8,215,164 B1 | 7/2012 | Hussain et al. | |
| 8,364,287 B2 | 1/2013 | Pearson et al. | |
| 8,803,683 B2 | 8/2014 | Schnitz et al. | |
| 8,836,467 B1 | 9/2014 | Cohn et al. | |
| 8,904,669 B2 | 12/2014 | Tichborne et al. | |
| 8,907,803 B2 | 12/2014 | Martin | |
| 8,918,091 B1 | 12/2014 | Hoelzle et al. | |
| 8,982,768 B2 | 3/2015 | Mills et al. | |
| 9,028,747 B2 | 5/2015 | Gill | |
| 9,791,429 B2 * | 10/2017 | Howes, Jr. | G01N 33/1813 |
| 2002/0087882 A1 | 7/2002 | Schneier et al. | |
| 2004/0020271 A1 | 2/2004 | Hutchinson | |
| 2004/0035584 A1 | 2/2004 | Gleim et al. | |
| 2004/0090345 A1 | 5/2004 | Hitt | |
| 2004/0104345 A1 | 6/2004 | Kansakoski et al. | |
| 2004/0250605 A1 | 12/2004 | Garritano | |
| 2005/0029903 A1 | 2/2005 | Tadayon et al. | |
| 2005/0167157 A1 | 8/2005 | Boyadjieff | |
| 2005/0270173 A1 | 12/2005 | Boaz | |
| 2006/0004593 A1 | 1/2006 | Seat et al. | |
| 2006/0137627 A1 | 6/2006 | Kim et al. | |
| 2006/0196254 A1 | 9/2006 | Fjerdingstad | |
| 2007/0012044 A1 | 1/2007 | Osborn et al. | |
| 2007/0051170 A1 | 3/2007 | Gardiner | |
| 2007/0103289 A1 | 5/2007 | Dagci | |
| 2008/0173273 A1 | 7/2008 | Cunningham | |
| 2009/0009297 A1 | 1/2009 | Shinohara et al. | |
| 2009/0038579 A1 | 2/2009 | Shieh et al. | |
| 2009/0076661 A1 | 3/2009 | Pearson et al. | |
| 2009/0102653 A1 | 4/2009 | McGinnis et al. | |
| 2009/0302782 A1 | 12/2009 | Smith | |
| 2009/0314384 A1 | 12/2009 | Brakefield et al. | |
| 2010/0008272 A1 | 1/2010 | Messinger et al. | |

| | | | |
|---|---|---|---|
| 2010/0026518 A1 | 2/2010 | Kirst et al. | |
| 2010/0033562 A1 | 2/2010 | Allds | |
| 2010/0059013 A1 | 3/2010 | Narayanakumar et al. | |
| 2010/0072368 A1 | 3/2010 | Boegli et al. | |
| 2010/0140246 A1 | 6/2010 | Grider et al. | |
| 2010/0207754 A1 | 8/2010 | Shostak et al. | |
| 2010/0241369 A1 | 9/2010 | Wicht et al. | |
| 2010/0268423 A1 | 10/2010 | Breed | |
| 2011/0125417 A1 | 5/2011 | Qing et al. | |
| 2011/0155084 A1 | 6/2011 | Sargeant et al. | |
| 2011/0166689 A1 | 7/2011 | Alden et al. | |
| 2011/0245696 A1 | 10/2011 | Yamashita et al. | |
| 2011/0298288 A1 | 12/2011 | Cho et al. | |
| 2012/0079830 A1 | 4/2012 | Rodriguez et al. | |
| 2012/0089299 A1 | 4/2012 | Breed | |
| 2012/0118822 A1 | 5/2012 | Strickland | |
| 2012/0125283 A1 | 5/2012 | Russo et al. | |
| 2012/0167845 A1 | 7/2012 | Sands et al. | |
| 2012/0192910 A1 | 8/2012 | Fowler et al. | |
| 2012/0199400 A1 | 8/2012 | Boulet et al. | |
| 2012/0268292 A1 | 10/2012 | Rock | |
| 2012/0296567 A1 | 11/2012 | Breed | |
| 2012/0312345 A1 | 12/2012 | Ward et al. | |
| 2013/0062288 A1 | 3/2013 | Spani | |
| 2013/0094430 A1 | 4/2013 | Mills et al. | |
| 2013/0125641 A1 | 5/2013 | Chemali et al. | |
| 2013/0134094 A1 | 5/2013 | Drew et al. | |
| 2013/0298642 A1 | 11/2013 | Gillette, II | |
| 2013/0298652 A1 | 11/2013 | Gillette, II | |
| 2013/0298664 A1 | 11/2013 | Gillette, II | |
| 2013/0298857 A1 | 11/2013 | Gillette, II | |
| 2013/0299000 A1 | 11/2013 | Gillette, II | |
| 2013/0299001 A1 | 11/2013 | Gillette, II | |
| 2013/0300341 A1 | 11/2013 | Gillette, II | |
| 2013/0300574 A1 | 11/2013 | Gillette, II | |
| 2013/0301674 A1 | 11/2013 | Gillette, II | |
| 2013/0304346 A1 | 11/2013 | Gillette, II | |
| 2013/0304351 A1 | 11/2013 | Gillette, II | |
| 2013/0304385 A1 | 11/2013 | Gillette, II | |
| 2013/0332257 A1 | 12/2013 | Scheinost et al. | |
| 2014/0041867 A1 | 2/2014 | Belgrave | |
| 2014/0102902 A1 | 4/2014 | Son et al. | |
| 2014/0116948 A1 | 5/2014 | Meyer | |
| 2014/0186210 A1 | 7/2014 | Gill | |
| 2015/0266753 A1 | 9/2015 | Fraim | |
| 2016/0168976 A1 * | 6/2016 | Zhang | G01M 3/26 |
| | | | 73/40.5 R |
| 2016/0252087 A1 * | 9/2016 | Wetherill | G08B 21/187 |
| | | | 73/168 |
| 2017/0040520 A1 | 2/2017 | Gillette, II | |
| 2017/0102308 A1 * | 4/2017 | Gillette | G01N 11/00 |
| 2019/0131607 A1 | 5/2019 | Gillette, II | |
| 2019/0137308 A1 * | 5/2019 | Bell | G01F 1/363 |
| 2019/0145658 A1 | 5/2019 | Hodgkinson | |

FOREIGN PATENT DOCUMENTS

| | | | | |
|---|---|---|---|---|
| EP | 0552833 | | 11/1996 | |
| EP | 1826735 | | 8/2007 | |
| GB | 2490938 A | * | 11/2012 | F16N 29/00 |
| WO | WO-2008157801 A2 | * | 12/2008 | B01L 3/502715 |
| WO | 2012130112 | | 10/2012 | |
| WO | 2013169942 | | 11/2013 | |
| WO | WO-2019056036 A1 | * | 3/2019 | G01N 1/14 |

* cited by examiner

METHODS AND DEVICES FOR MONITORING MACHINE FLUIDS

CROSS-REFERENCE TO RELATED APPLICATIONS

This application is a continuation application of and claims priority to U.S. patent application Ser. No. 17/160, 366, entitled "METHODS AND DEVICES FOR MONITORING MACHINE FLUIDS" which was filed on Jan. 27, 2021 (the "'366 application"). The '366 application claims priority to and the benefit of U.S. Provisional Patent Application No. 62/966,484, entitled "METHODS AND DEVICES FOR DETERMINING MACHINE FUNCTION" filed on Jan. 27, 2020. The foregoing applications are hereby incorporated in their entirety by reference for all purposes.

BACKGROUND

As used herein, the term "fluid" refers to any fluid used in machinery, such as oil, grease, brake fluid, steering fluid, hydraulic fluid, coolant, air conditioning fluid, or cleaning fluid. Machinery (e.g., engines, compressors, gearboxes, grinding mills, pumps) use fluids for various reasons, such as to reduce the friction between moving mechanical components. Ongoing maintenance and preventative care of machinery often requires gathering and analyzing samples of fluids to determine their amount of degradation. Degradation can be as a result of, but not limited to, contamination water (e.g., free water, condensing moisture), diti (e.g., dust, sand), wear metals (e.g., copper, tin, iron, lead, chrome) resulting from metal-to-metal surface frictional wear, soot (carbon), engine coolant leakage or contamination, or contamination by chemical constituents stemming from internal combustion process.

Some fluid contaminants, such as particles (from wear and/or debris) cannot be accurately measured statically when the machine containing the fluid is turned off. Additionally, hydraulic fluid or coolant may be in a closed-loop system connected to the machine, and it is typically not actively monitored for degradation and performance.

Further, drawing fluid samples improperly, or without sufficient frequency, can compromise the accuracy of fluid testing, condition, and remaining-useful-life ("RUL").

In some cases fluid quality is estimated using empirical data that is tied to an expected lifetime of the fluid based upon performance parameters of the machinery. In those cases, a monitoring system measures the performance of a component in the machine, e.g., speed, acceleration, deceleration, and/or other and, based upon the performance, estimates a time at which the fluid will degrade in quality.

Consequently, there is a need for a device (or system) that accurately monitors fluid conditions in machinery to help avoid machine damage or failure.

SUMMARY

A device as disclosed herein is mounted to a machine to monitor fluid in the machine and to potentially take fluid samples for testing.

A device according to this disclosure could be modular or integrally formed, and includes (1) a cover (or top) that has a printed circuit board control assembly (also called a PCBA, PCB, controller, or edge computing device), and (2) a spacer that includes a power connector for connecting to a power source, optionally one or more additional connectors for connecting to external sensors, and optionally an external antenna connector. The device may also include a manifold having a fluid path through which the fluid being monitored can flow. If a manifold is used it preferably includes a fluid pressure sensor and fluid temperature sensor that each communicate with the PCBA.

The device may also include a valve in communication with the fluid path through the manifold. The valve is normally in a first, closed position, but can be moved to a second, open position by the PCBA to allow fluid to flow into a sample bottle attached to the manifold.

The device could also include a manifold block attached to the manifold, wherein fluid flows through the manifold block and into the manifold, and out again through the manifold block. A manifold block, if used, preferably contains one or more fluid sensors to measure any one or more fluid parameters discussed herein. Hence, fluid parameters can be measured by sensors remote to the device and communicated to the PCA by wired connections to connectors in the spacer, or transmitted wirelessly to the PCBA, or measured by the device by sensors in the manifold or manifold block and communicated by wired or wireless connections to the PCBA.

The PCBA may analyze and/or store information received from the one or more sensors and send signals based on the information. For example, the PCBA may activate a warning signal, such as a colored or flashing light for an operator, activate the valve in order to take a fluid sample, turn off the machine, turn off a component of the machine (such as hydraulics to raise and lower a truck bed), limit the speed of operation of the machine, schedule the machine for immediate maintenance or maintenance within a given time frame, or other.

The PCBA may communicate with a central controller (also called a server or central server) remote to the device, such as at an office where operators can monitor the machine on which the device is mounted. The central controller could analyze the data received from the PCBA and send signals to the machine directly, or through the PCBA, to perform one or more of the functions described in the preceding paragraph or any other suitable function.

The central controller could also receive information from multiple devices mounted, respectively, on other machines of the same type and establish base-line fluid operating parameters for a fleet. If a measured fluid parameter from one machine is outside of a base-line parameter, the central controller could signal the PCBA on the device for that machine to take one of the actions discussed previously or any other suitable action.

The fluid parameters monitored could be one or more of viscosity, temperature, pressure, density, dielectric constant, water content, flow rate, consumption rate, total acid number (TAN), total base number (TBN), oxidation numbers, nitration levels, oil SAE grade, the quantity of wear particles shed off the machine, and/or contamination particles (such as sand). The fluid sensors may be optical sensors and may comprise a data sampling rate of up to 20 kHz.

The sensors may also be, or be in addition to the optical sensors, other types of sensors, such as internet of things (IoT)-enabled sensors in communication with the PCBA, which could also monitor machine vibration, operational RPM torque levels, and other desired parameters.

The device is powered by AC or DC power provided in any suitable manner, such as by the machine being monitored, a battery, or a solar cell(s).

The sensor readings may be date and time-stamped using a GST time-stamping system. This allows for identification of the timescale of monitored parameters, and also allows for correlation to other data sources, such as a SC ADA system.

Data may be communicated to the PCBA and/or central controller periodically, such as in 30-second intervals, or continuously over a wireless link.

For the purposes of measuring fluid parameters, metrics may be displayed in terms of percent change from a "nominal" value, which is the value of new fluid before being used in the machine.

If the fluid condition reveals a potentially dangerous trend or condition in any measured parameter(s) the device may automatically fill a sample bottle and/or notify service personnel via email, and SMS messaging, or in any suitable manner. The message may be to collect the appropriate sample bottle(s) from a device on the machine.

The accumulation of foam in fluid may result in undesirable behavior and premature degradation. To suppress surface foam formation, foam inhibitors (defoamant additives) are sometimes compounded into the fluid. A device according to this disclosure could activate a pump to add more additives to a fluid if the measured additive amount is low.

Further, the ability to monitor a machine before and after a fluid change can help determine a baseline for fluid parameters and could potentially indicate the amount of varnish, sludge or other residual contaminants contained in the new fluid. Base lining can be used to re-calibrate the monitoring parameters and re-define triggers for alerts, taking samples, and/or to determine an appropriate interval for fluid sampling.

U.S. Pat. No. 10,466,152 is incorporated herein by reference.

BRIEF DESCRIPTION OF THE DRAWINGS

FIG. 14 is an opposite side, assembled view of the device of FIG. 1 without an external antenna.

DETAILED DESCRIPTION

Figure 1:
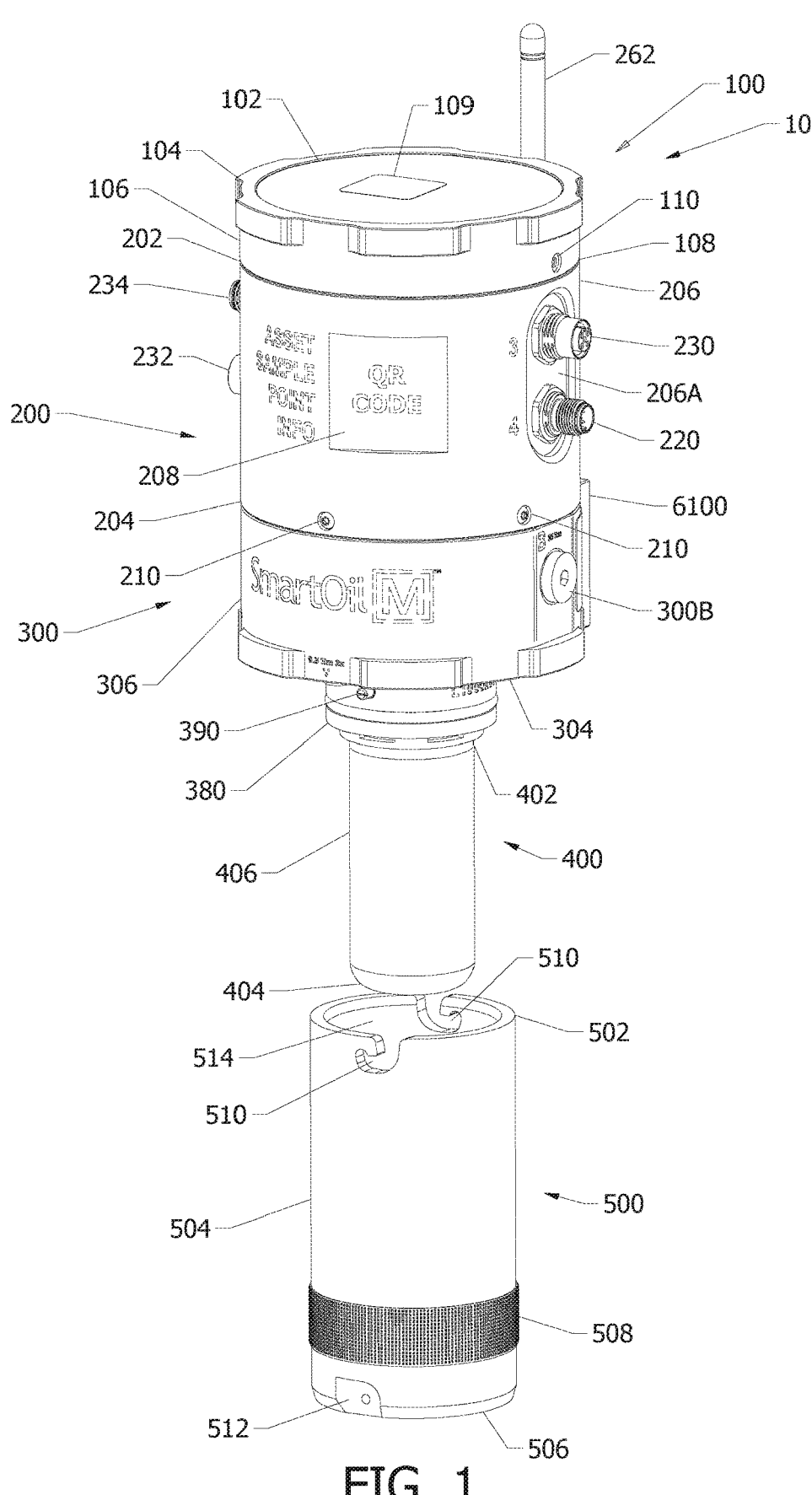
FIG. 1 shows a front, perspective, partially exploded, front view of a device according to this disclosure.

Turning now to the drawings where the purpose is to describe embodiments of the invention and not to limit same, FIG. 1 shows a device 10 according to this disclosure. Device 10 as shown includes a cover 100, a spacer 200, a manifold 300, a manifold block 6100, a sample bottle 400, and a protective container 500. As shown, cover 100, spacer 200, manifold 300, and manifold block 6100 are separate components that are attached. An advantage of this modular design is that different covers, spacers, manifolds, and/or manifold blocks can be substituted depending on the use, environment, cost considerations, or any functional aspect desired by a customer. Alternatively, any two or more of the components may be a single, integral piece. For example, any of the following may be formed as a single piece: (1) the cover and spacer, (2) the spacer and manifold, (3) the manifold and manifold block, (4) the cover, spacer, and manifold, (5) the spacer, manifold and manifold block, or (6) the cover, spacer, manifold, and manifold block.

The purpose of a device according to this disclosure is to monitor one or more parameters of a fluid used in a machine, assist in determining the condition of the fluid, and potentially altering the operation of the machine or sending a communication based on the measured parameter(s). A machine may have multiple devices installed on it to monitor multiple fluids.

Cover

Cover 100 (or first module), shown for example in FIGS. 1, 11-15, and 17-19 has a top surface 102, an outer rim 104, an outer surface 106, a bottom rim 108, a display (which can also include a user control) 109, and openings 110 to receive anchoring screws (not shown) to firmly attach cover 100 to a spacer, such as spacer 200 (or second module) shown in FIG. 1.

Figure 27:
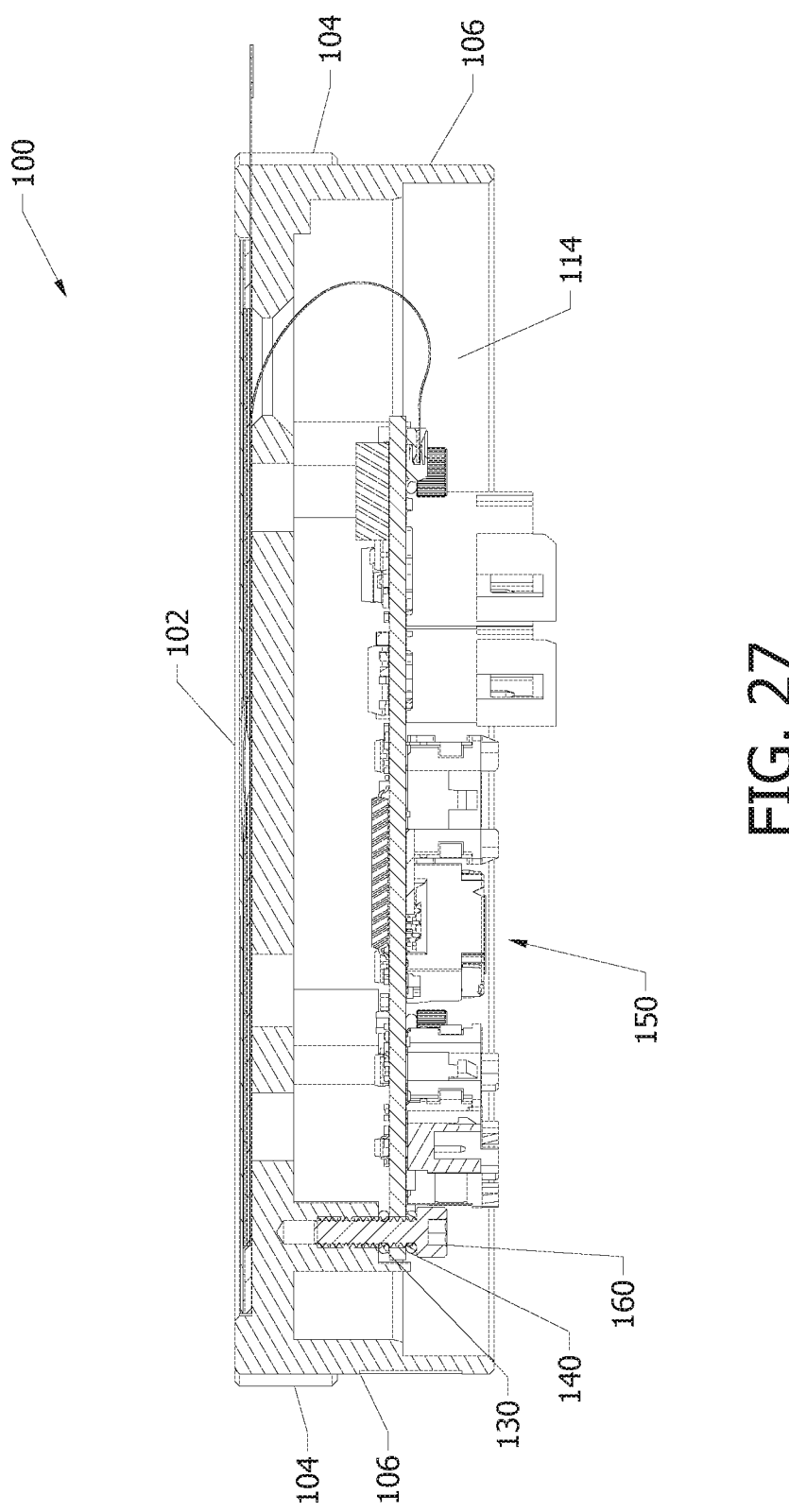
FIG. 27 is a side, partial cross-sectional view of a cover according to this disclosure.

Cover 100 has a cavity 114, best seen in FIG. 27, that retains a printed circuit board assembly (also called a PCBA, PCB, processor, or edge computing device) 150, which is configured to receive input from one or more of (1) device 10 or any device according to this disclosure, (2) one or more captive or remote sensors, and (3) a central controller. PCB 150 may also control the operation of device 10 or any device according to this disclosure.

PCBA 150 may also analyze or store data it receives and may transmit and/or receive data from a central controller remote to the device. PCBA 150 may be configured to control the function of device 10, such as by opening a valve to collect a fluid sample (discussed further below), or alert an operator (either remote to or at the machine on which the device is mounted), or to turn the machine off, govern the speed of the machine, or preventing certain aspects of the machine, such as the hydraulics for a truck bed, from operating.

Figure 2:
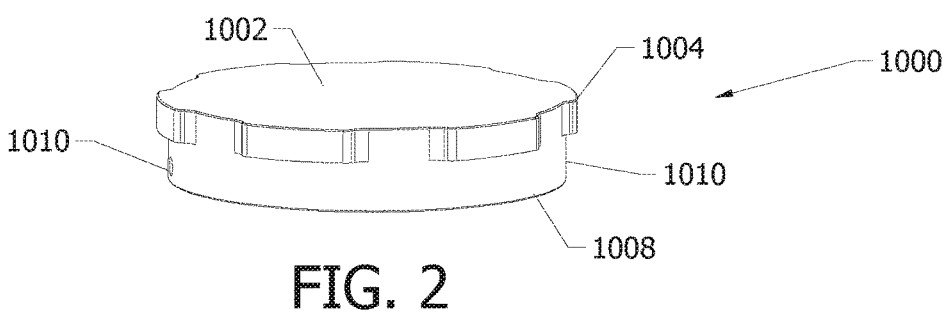
FIG. 2 is a front, perspective view of a cover according to this disclosure.

An alternate cover 1000 is shown in FIG. 2. It is the same as cover 100 except that it does not include a display and/or user control, which reduces costs if a display and/or user control is unnecessary or not desired by the customer.

Figure 19:
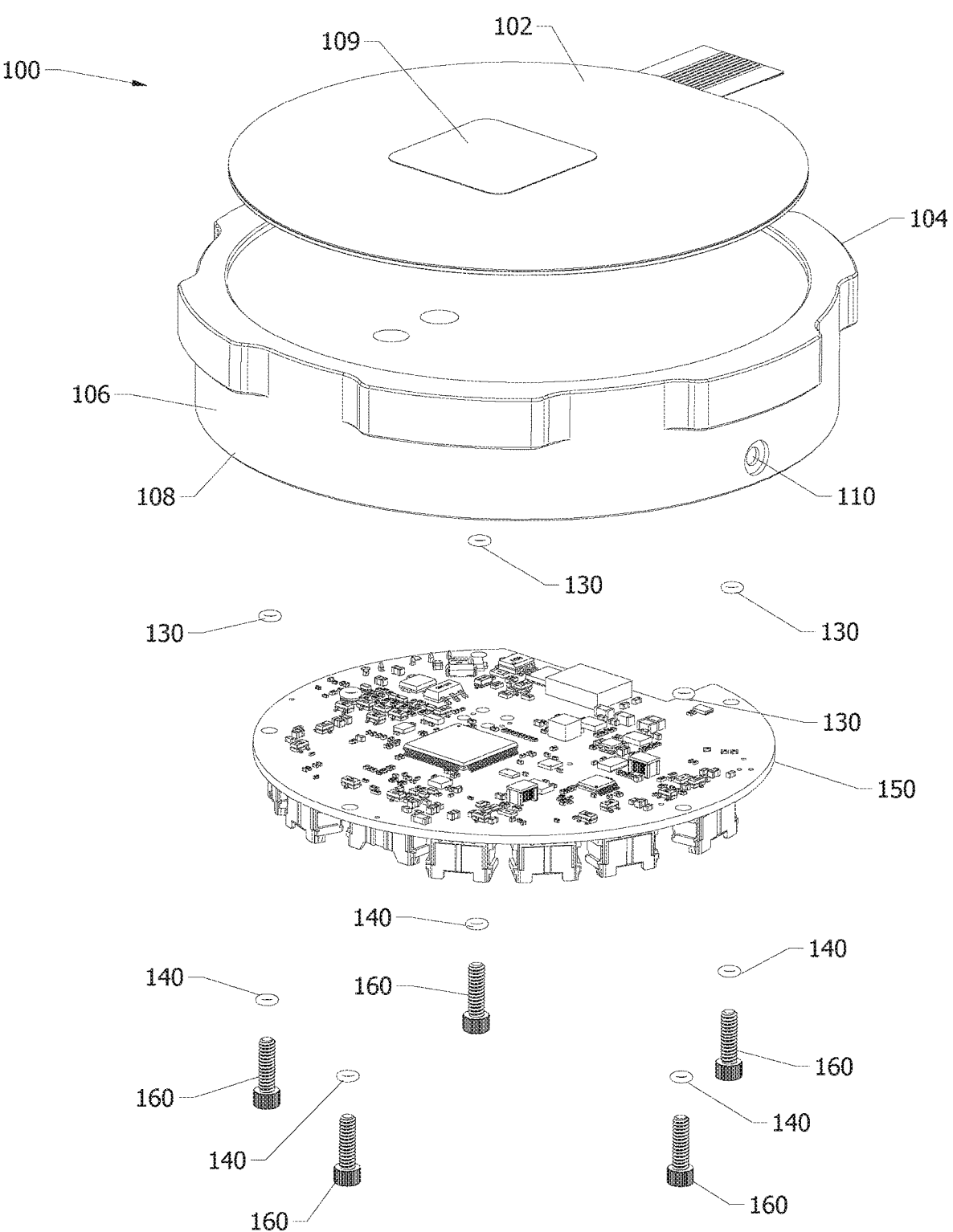
FIG. 19 is a front, perspective, exploded view of the cover of FIG. 1.

As best seen in FIG. 19, the top surface 102 of cover 100 is preferably a separate disk attached to the body 111 of cover 100. PCBA 150 is mounted in cavity 114 (as shown in FIG. 27) by fasteners 160. Spacers 130 are positioned above PCBA 150 and spacers 140 are positioned below PCBA 150. Each fastener 160 passes through a spacer 140, through PCBA 150, through a spacer 130 and are then threaded into a boss in cover 100 or cover 1000. The spacers 130 and 140 help cushion PCBA 150 from vibration while the machine is operating.

Spacer

The spacer (or second module), whether a separate module or formed integrally with one or more other components, comprises a housing defining an inside cavity 211. The spacer has a power connector 220 with a first end configured to connect to a power source. The power connector 220 has a second end configured to be connected to an internal wire (or any structure suitable for transferring power) in the spacer cavity 211. The wire connects to the PCBA 150 (which can control a solenoid, as described below, for opening a valve if the device includes a valve). The spacer may also have any number of connectors for connecting to various remote sensors that measure, for example, fluid temperature, fluid viscosity, fluid particulate level, fluid contaminants, machine vibration, or any fluid parameters. The measurements are transferred through a spacer connector, preferably via a wired connection, to the PCBA 150. Alternatively, the measurements may be transferred through a wired or wireless connection directly to a central controller that is remote to the device.

Turning to FIG. 1, a spacer 200 has an top edge 202, a bottom edge 204, an annular outer surface 206 that preferably includes a QR code 208, and openings 210, which receive fasteners (such as set screws, not shown) that help secure spacer 200 to a manifold, such as manifold 300. Top edge 202 is where the bottom edge 108 of cover 100, or the bottom edge 1008 of cover 1000, rests when the cover 100 or 1000 is positioned on the spacer.

Spacer 200 has a power connector 220 and three sensor connectors, 230, 232, and 234. Spacer 200 can have any number of sensor connectors positioned at any suitable position on spacer 200, or on any spacer according to this disclosure. Preferably one or more flat surfaces 206A are formed on spacer 200 in order to better seat washers and fasteners used to connect the sensor connectors and power connector to the spacer 200 or any spacer according to this disclosure.

Figure 3:
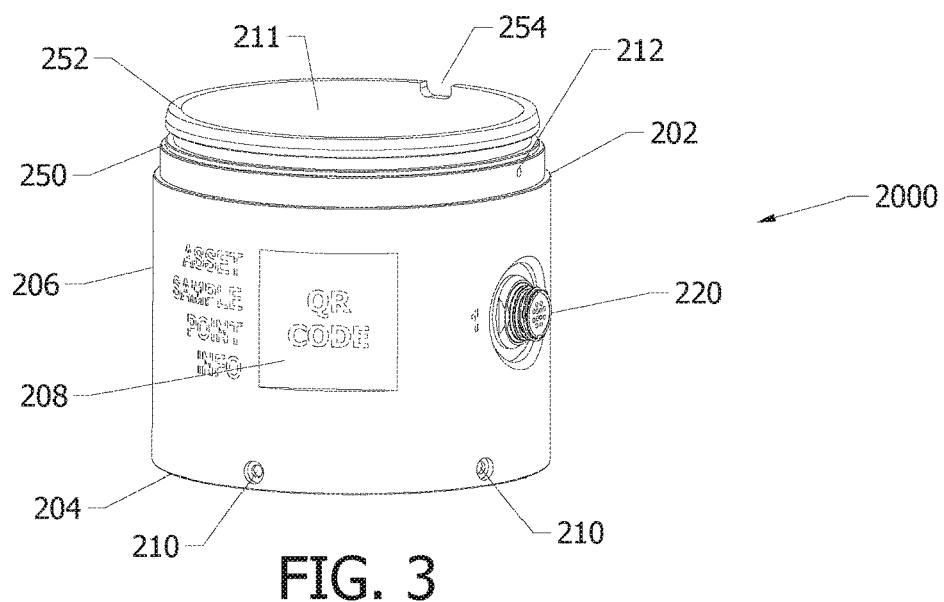
FIG. 3 is a front, perspective view of a spacer according to this disclosure.

An alternate spacer 2000 is shown in FIG. 3. Spacer 2000 has the same structure as spacer 200 except that it has only a power connector 220 and has no sensor connectors.

Figure 4:
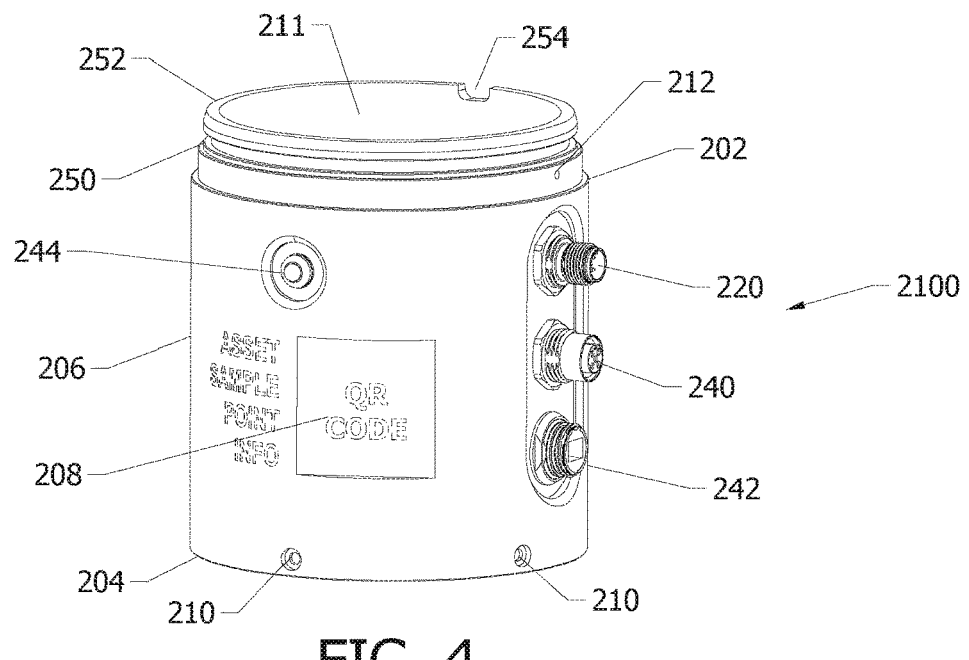
FIG. 4 is a front, perspective view of an alternate spacer according to this disclosure.

FIG. 4 shows another alternate spacer 2100 that has the same structure as spacer 200 or 2000 except that it has a power connector 220 and two sensor connectors 240, 242 in line vertically with power connector 220 and a light, such as an LED, 244. Light 244 can be controlled by the PCBA or a central controller to change color and/or blink to indicate various conditions. For example, if light 244 is green that may indicate that the fluid being monitored is within safe operating parameters. A yellow color may indicate a warning that one or more fluid parameters is close to an unacceptable level, and red or a flashing light may indicate a dangerous situation and/or that immediate maintenance is required.

A QR code 208 is preferably attached to the spacer, although it can be located at any suitable location on the device.

Spacers 2000 and 2100 have the same structure above upper lip 202, which is the same structure (not shown) on spacer 200 in FIG. 1. An upper, annular rim 252 includes a key way 254 that aligns with a matching projection (not shown) in cover 100 or cover 1000 to properly position the cover on the spacer. A groove 250 receives an o-ring (not shown), wherein the o-ring has a thickness great enough so the o-ring extends outward past groove 250. When cover 100 or 1000 is properly aligned with the top of a spacer 200, 2000, or 2100, it is pressed down over the o-ring, which creates an interference fit that helps seal out particles and moisture. Openings 212 receive fasteners (not shown) that pass through openings 110 in the cover to secure the cover to the spacer.

Figure 12:
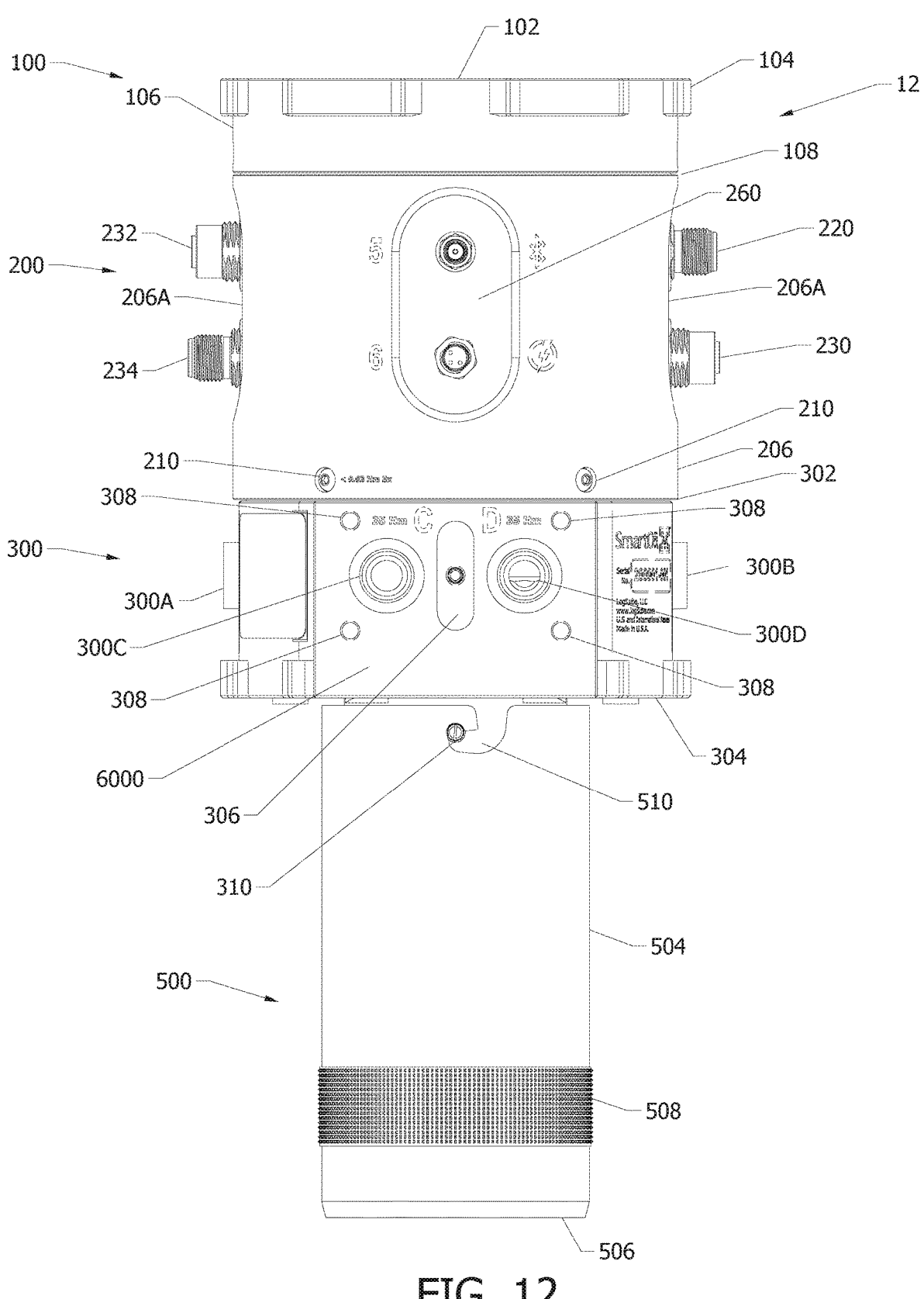
FIG. 12 is a back, assembled view of the device of FIG. 1 without an external antenna.
Figure 13:
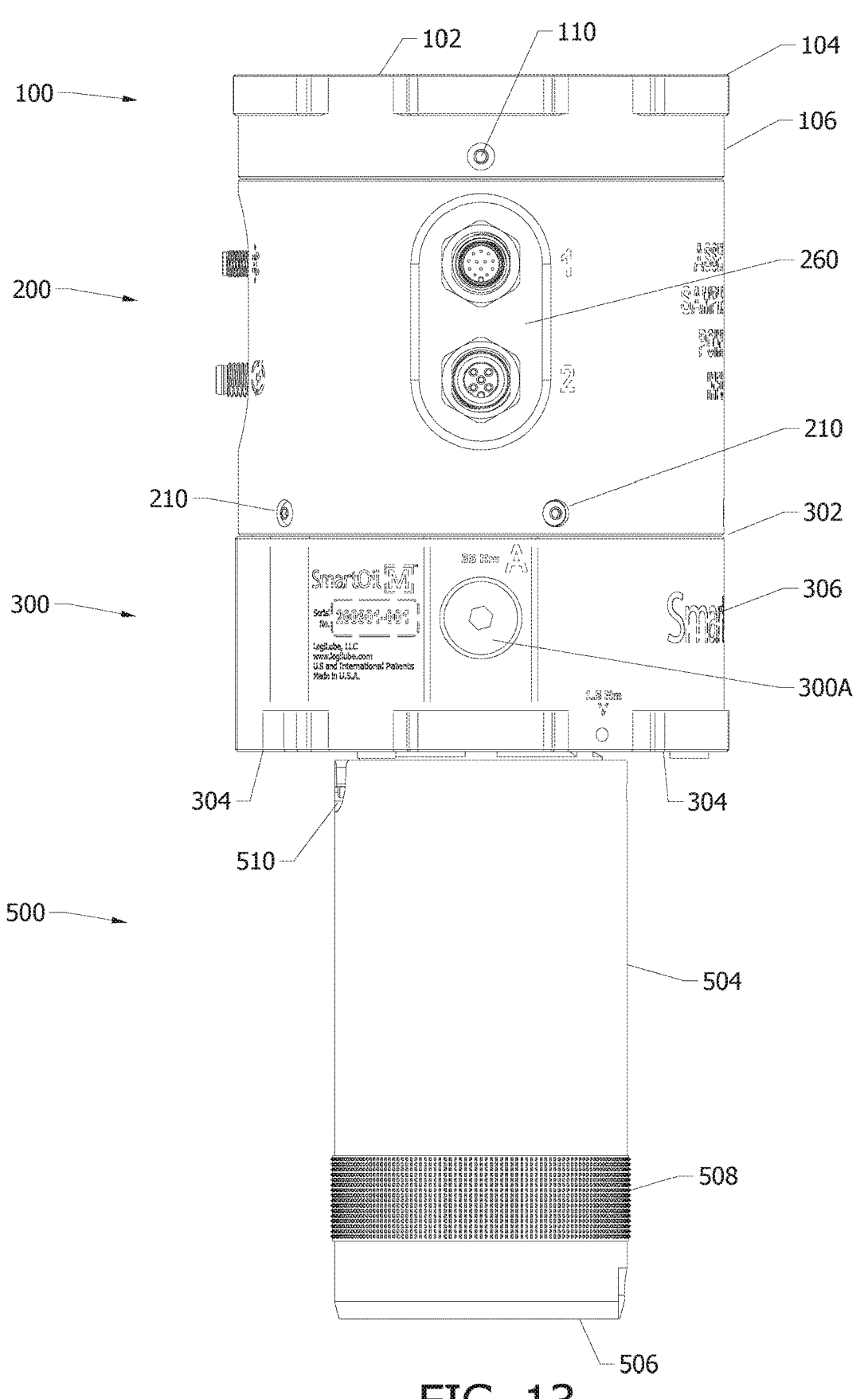
FIG. 13 is a side, assembled view of the device of FIG. 1 without an external antenna.
Figure 14:
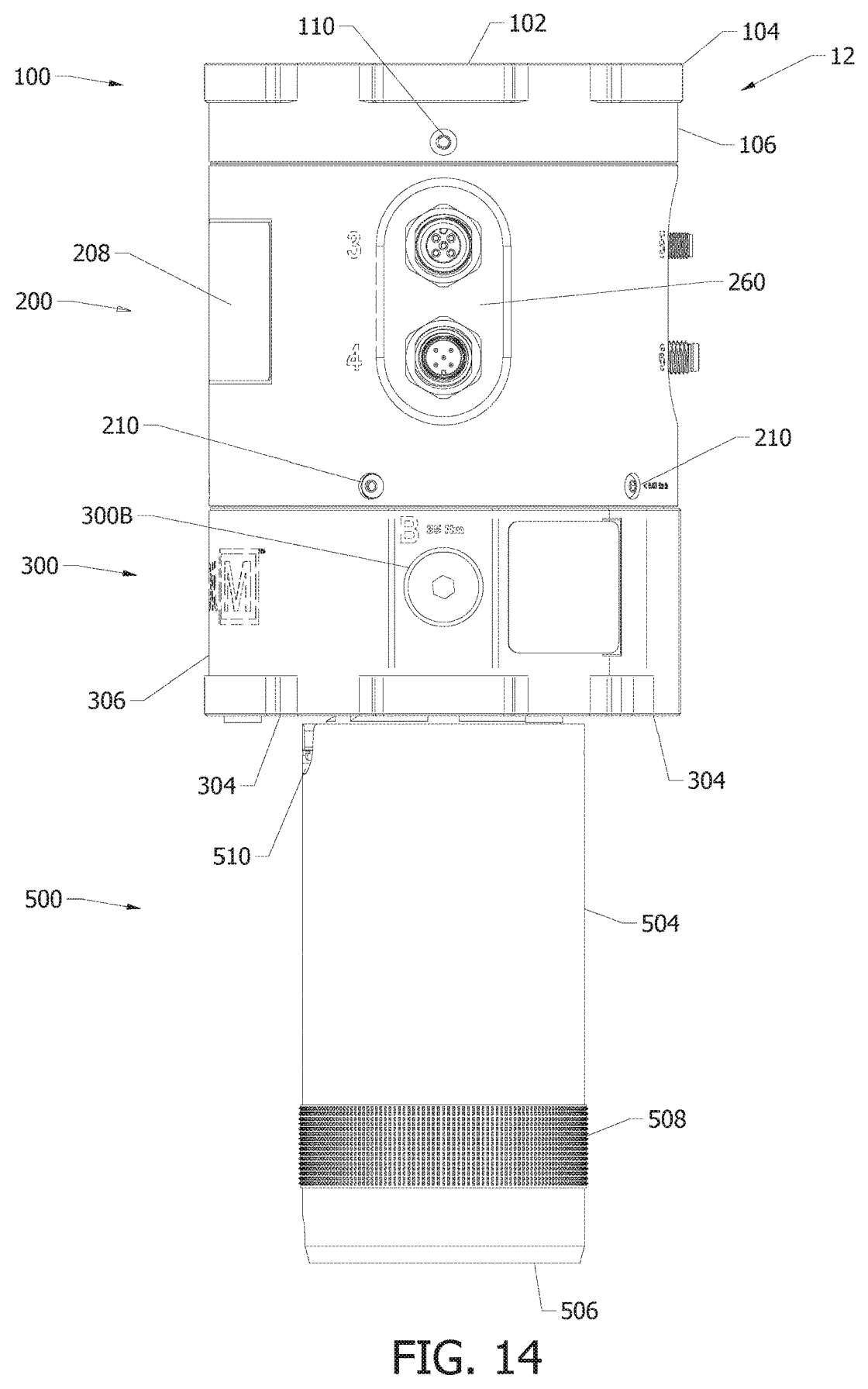
Figure 15:
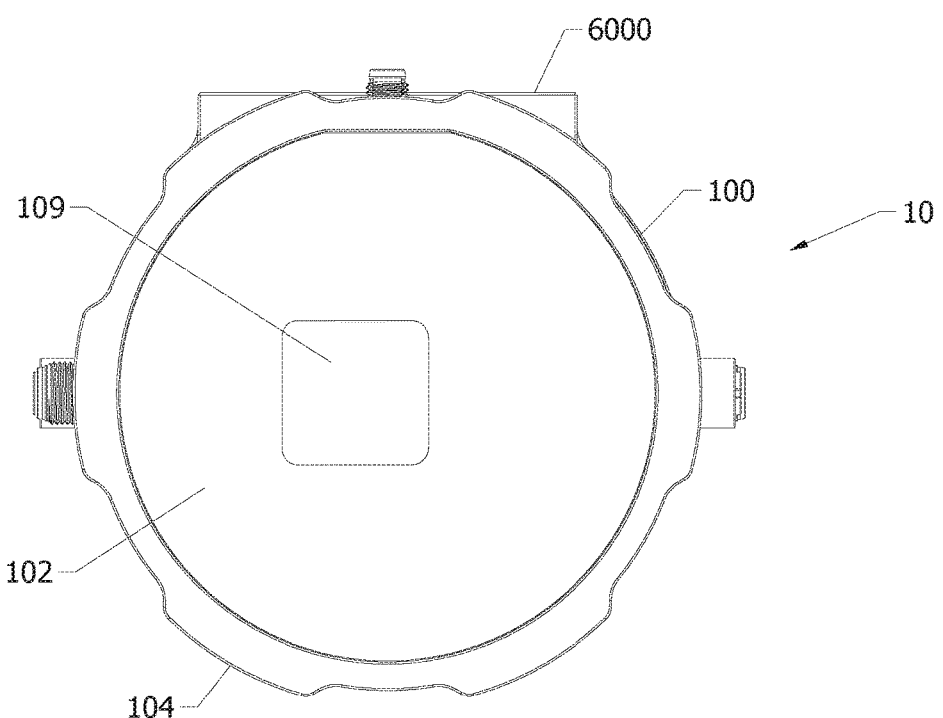
FIG. 15 is a top view of the device of FIG. 1.
Figure 16:
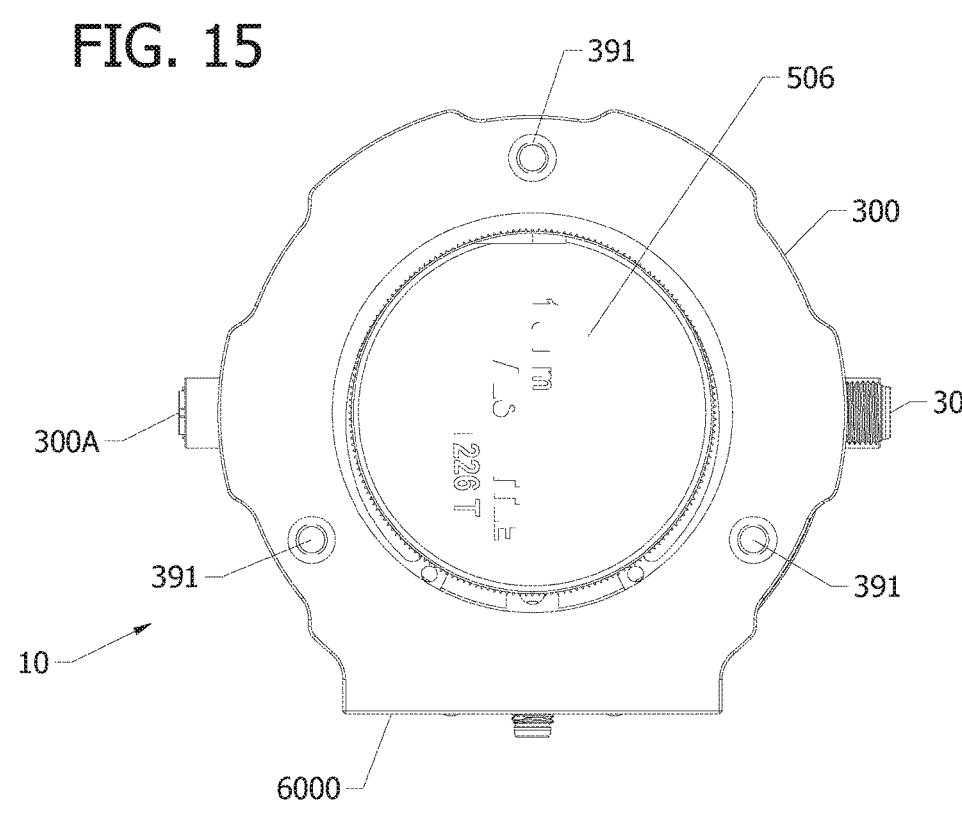
FIG. 16 is a bottom view of the device of FIG. 1.
Figure 17:
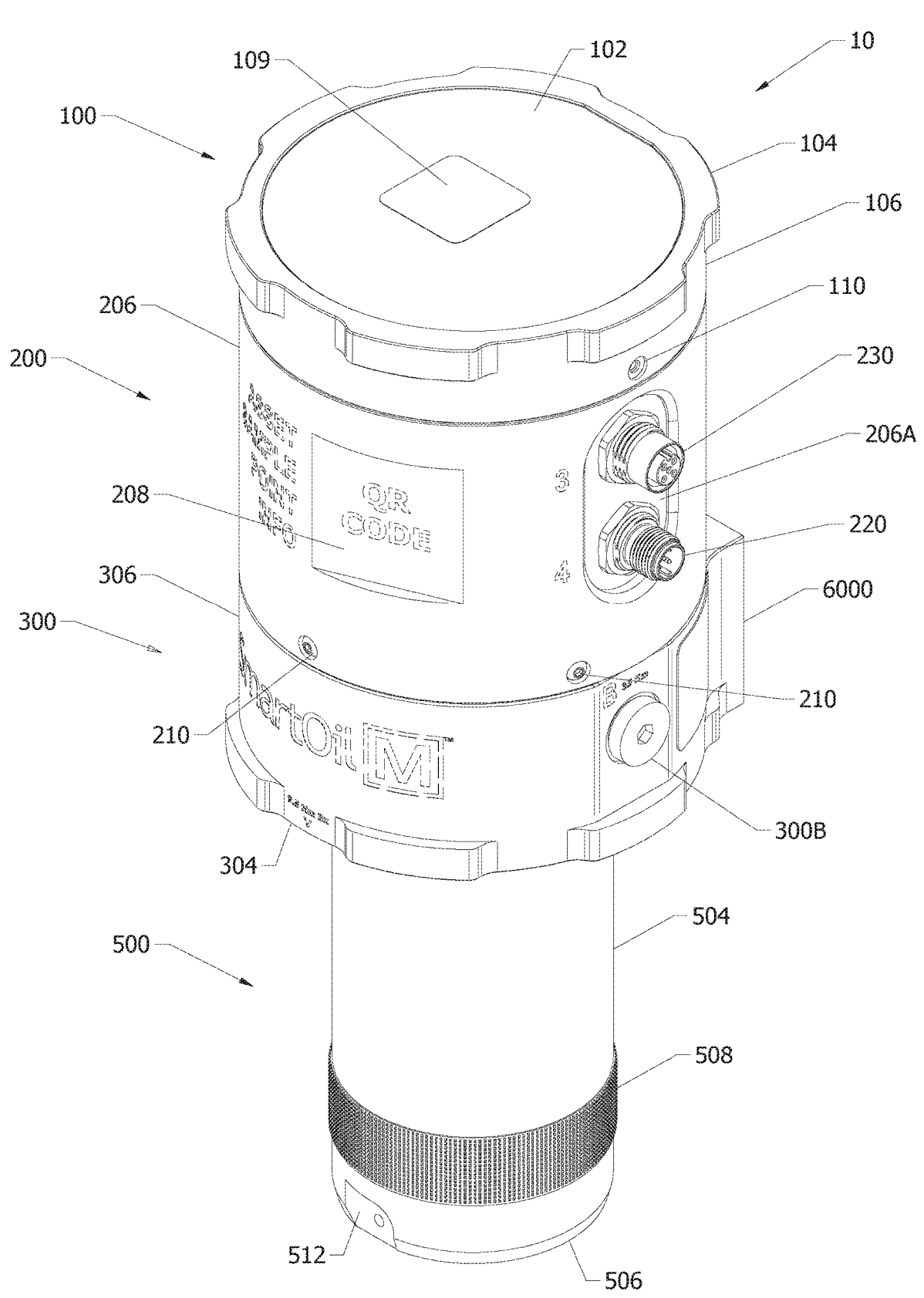
FIG. 17 is a side, perspective, assembled view of the device of FIG. 1 without an external antenna.

As shown, for example, in FIGS. 12-14, a spacer according to this disclosure may include an external antenna connector 260 to connect to antenna 262, which can send signals from PCBA 150 or receive signals for PCBA 150. An alternative external antenna connector 260A is shown in FIG. 28.

Figure 20:
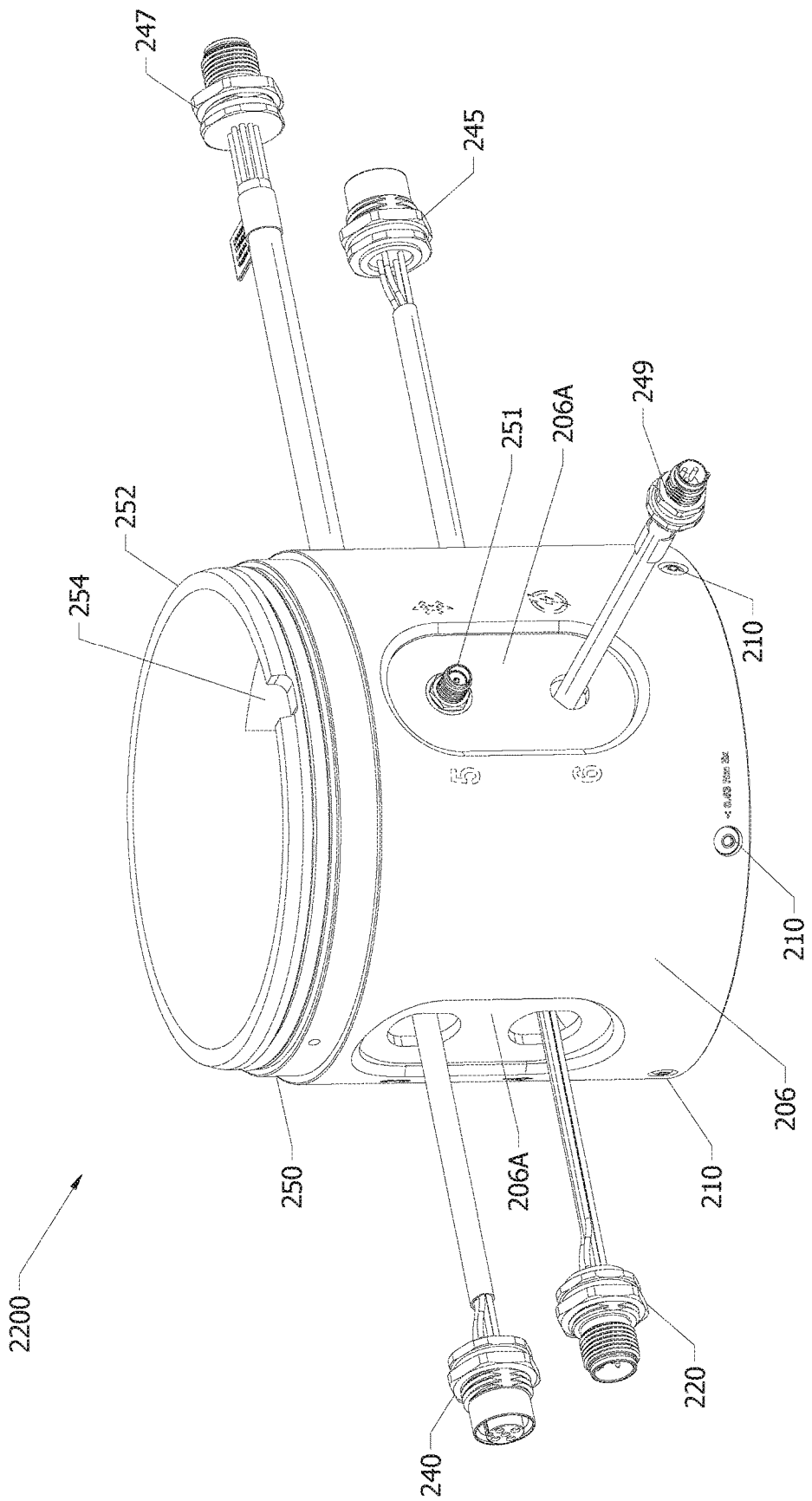
FIG. 20 is a side, perspective, exploded view of an alternate spacer according to this disclosure.
Figure 21:
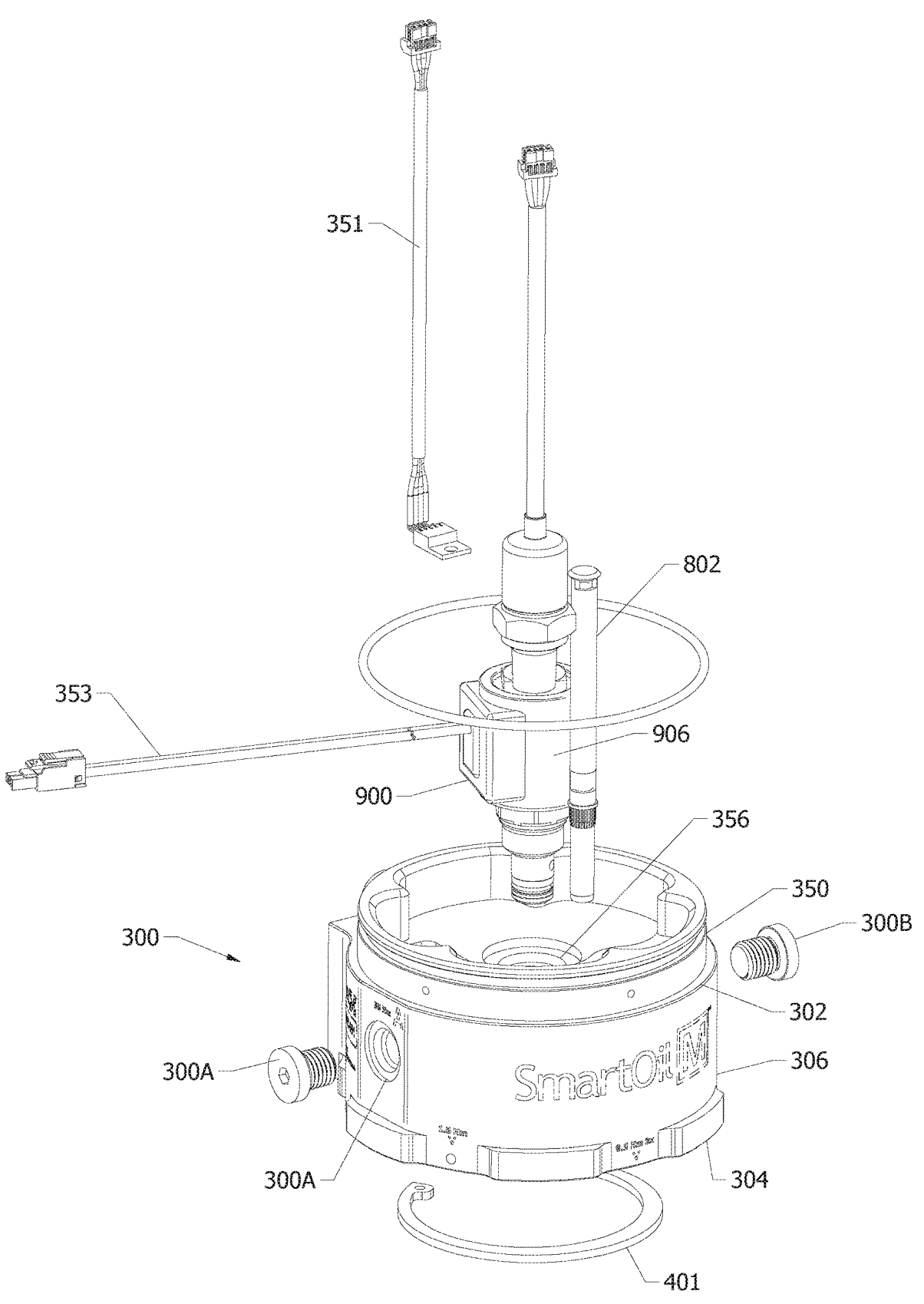
FIG. 21 is a front, perspective, exploded view of the manifold of FIG. 1.

Another alternate spacer 2200 is shown in FIG. 20. Spacer 2200 has the same structure as the previously described spacers except that it has different and more connectors 240, 245, 247, 249, and 251 to connect to wires that are connected to sensors to collect fluid data or other information, such as vibration, concerning the condition of the machine that the device is monitoring. Each spacer has a cavity 211 that is configured to retain wires that are connected at one end to a connector on the spacer and are connected at the opposite end to the PCBA 150. Cavity 211 also retains part of the valve structure (if a valve structure is used), which is explained further herein.

Figure 28:
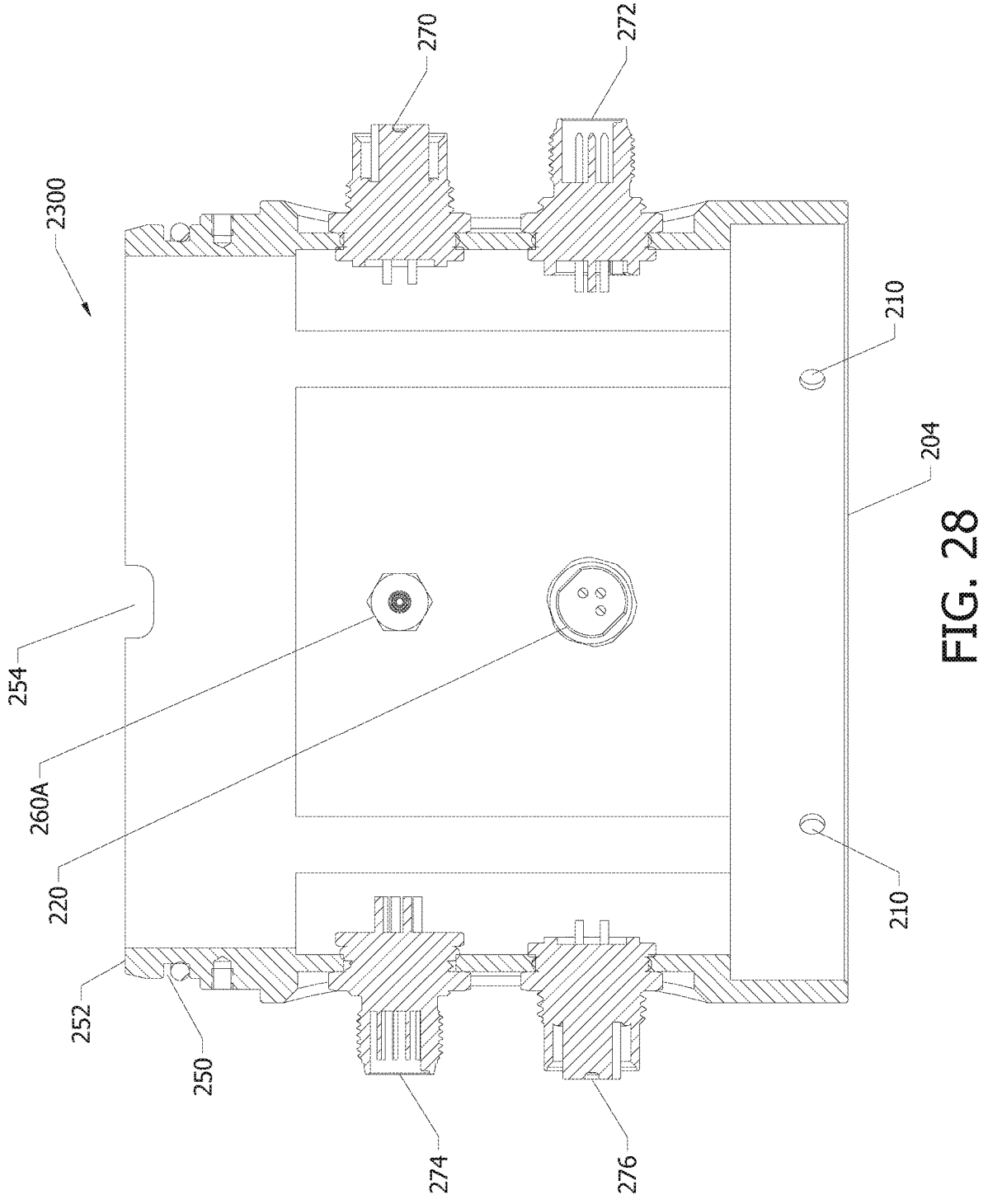
FIG. 28 is a side, cross-sectional view of an alternate spacer according to this disclosure.

Another alternative spacer 2300 is shown in FIG. 28. Spacer 2300 is the same as the previously described spacers except that it has alternate external antenna connector 260A and sensor connectors 270, 272, 274, and 276.

Manifold

A manifold 300 (or third module) is shown, for example, in FIGS. 1, 11-14, 17-18, 21, 24, 25A, and 26. Manifold 300 can serve the purpose of (1) directly monitoring one or more fluid parameters and include a passage for fluid to flow through it, (2) housing part or all of a valve assembly (if a valve assembly is used), (3) connecting to an optional manifold block, and (4) including sample bottle support structure 380 that supports and retains a sample bottle 400 and protective cannister 500 for the sample bottle (if used), and that also includes all or part of a pathway to vent the spacer cavity 211, and all or part of a pathway to vent the air from a sample bottle 400 when the bottle 400 is filled with sample fluid.

As shown, manifold 300 has a top edge 302, a bottom 304, and an outer surface 306. Manifold 300 as shown has a first fluid port 300A, a second fluid port 300B, a third fluid port 300C, and a fourth fluid port 300D. Alternatively, manifold 300 may only have two fluid ports, or may have no fluid ports if all fluid measurements are taken by remote sensors, or by sensors in the manifold block, and/or if no fluid samples are taken by the device.

Figures 25, 25A:
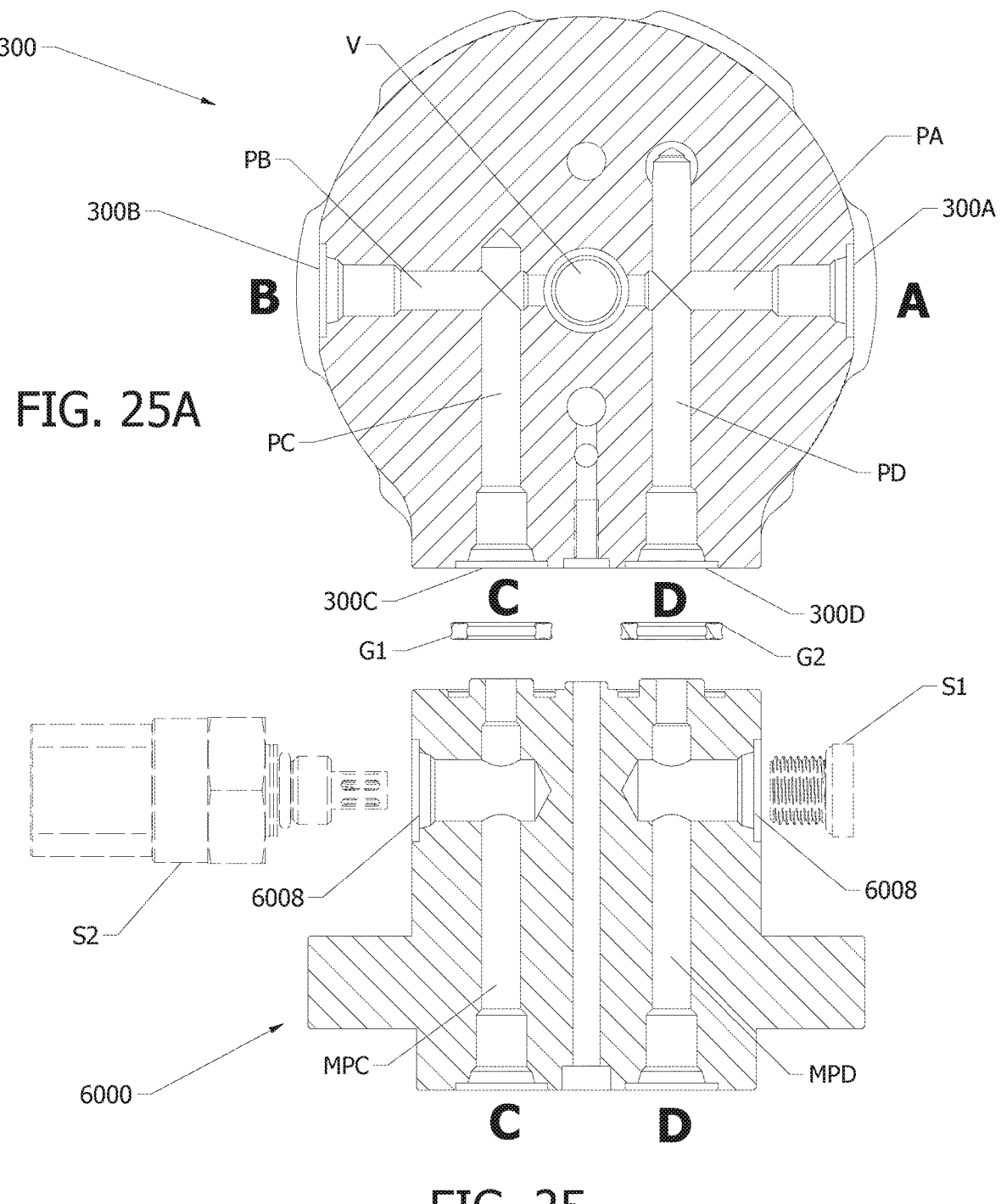
FIG. 25 is a cross-sectional, top view of the manifold block of FIG. 6 taken through line A-A.
FIG. 25A is a cross-sectional, top view of the manifold of FIG. 18 taken through line B-B.

If the manifold has two or more fluid ports, it also has an internal fluid pathway P, such as PA, PB, PC, and PD, as shown in FIG. 25A. If fluid flows through manifold 300 preferably only two of fluid ports 300A, 300B, 300C, 300D are open and the other two ports are blocked, such as by threading a bolt or other fastener into the port to block it. Fluid may flow in any suitable manner through the fluid path, such as from port A to port B, from port C to port D, from port B to port C, from port A to port C, or in any other manner.

If manifold 300 is configured for fluid to flow through it, it preferably includes at least two sensors—a fluid pressure sensor and a fluid temperature sensor. These sensors are in communication with PCBA 150 and, if a fluid sample is taken, the PCBA 150 determines the length of time to open the valve assembly, based on information received from the sensors and the volume of the sample desired, in order to collect the proper sample size in the sample bottle.

Pathway P may have an opening V as shown in FIG. 25A, which permits fluid to pass into a sample bottle when a valve structure is operated to open a valve, as discussed further herein.

Figure 18:
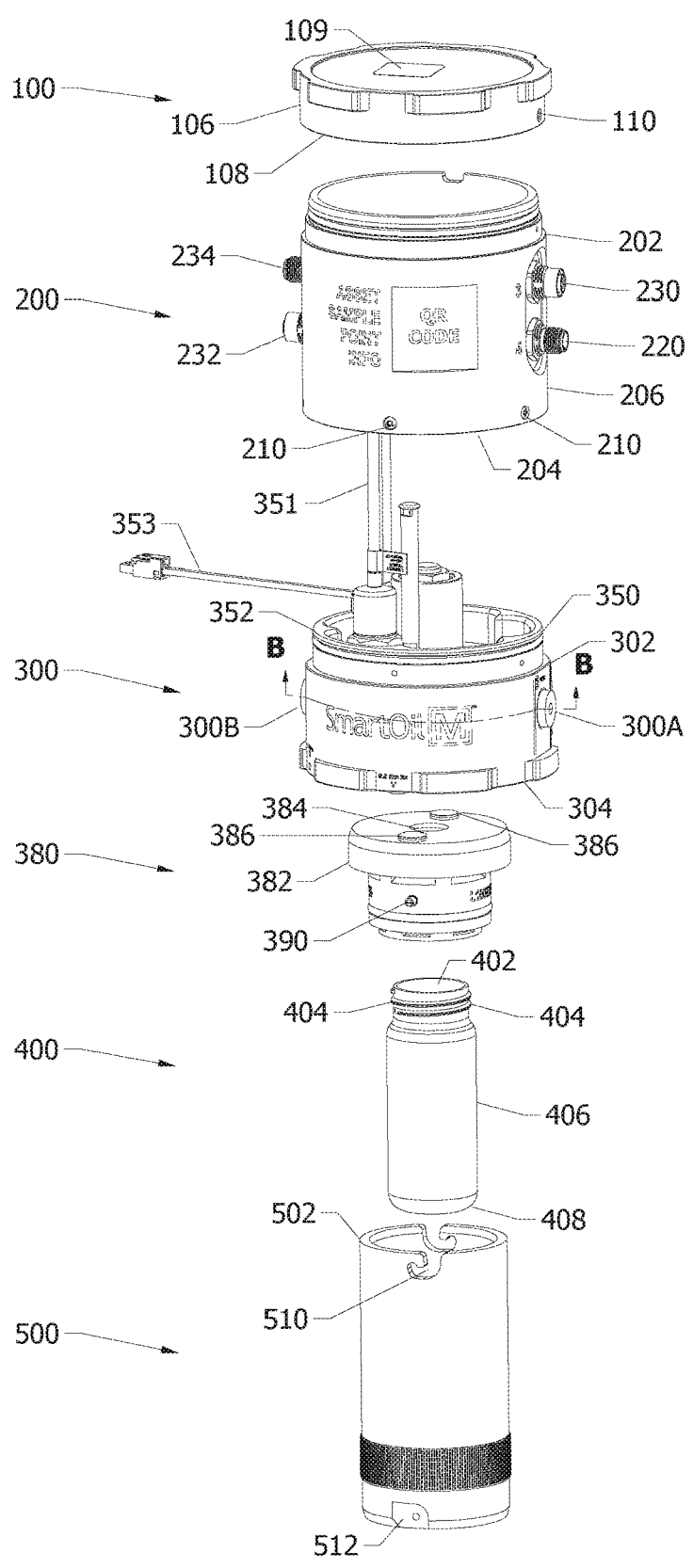
FIG. 18 is a front, perspective, exploded view of the device of FIG. 1 without an external antenna.

As shown, for example, in FIG. 18, manifold 300 has an upper lip 302 on which bottom edge 204 of spacer 200 rests when the two are connected. Manifold 300 further comprises an upper ledge 352 and a gap 350 that is configured to receive an o-ring (not shown). The o-ring is wide enough that it extends outward past gap 350. The spacer is pressed onto the top of manifold 300 and over the o-ring. This creates a compression fit that seals the interior of the spacer and the manifold against environmental contamination such as dust or moisture. When the spacer is seated on the manifold, fasteners (not shown) are passed through openings 210 and received in openings 313 to secure the spacer to the manifold.

Sample Bottle Mounting Structure

Sample bottle mounting structure 380 is configured to retain a sample bottle 400 and a protective container 500. Structure 380, best seen in FIGS. 18 and 24 (in cross section) has a top cap 382 with an opening 384 to a passageway 356 which communicates with sample bottle opening 402. Structure 380 connects to manifold 300 and includes threads 358 that receive threads 404 of bottle 400 so bottle 400 can be threaded onto structure 380. Beneath threads 358 is an o-ring 360 in groove 362. The o-ring applies compressive force to the neck of sample bottle 400 to help prevent it from loosening and unthreading during operation of the machine to which the device is attached.

Structure 380 also includes two rods, bolts, or other structures 390 that connect to and retain the protective cannister (or protective container) 500.

Figure 22:
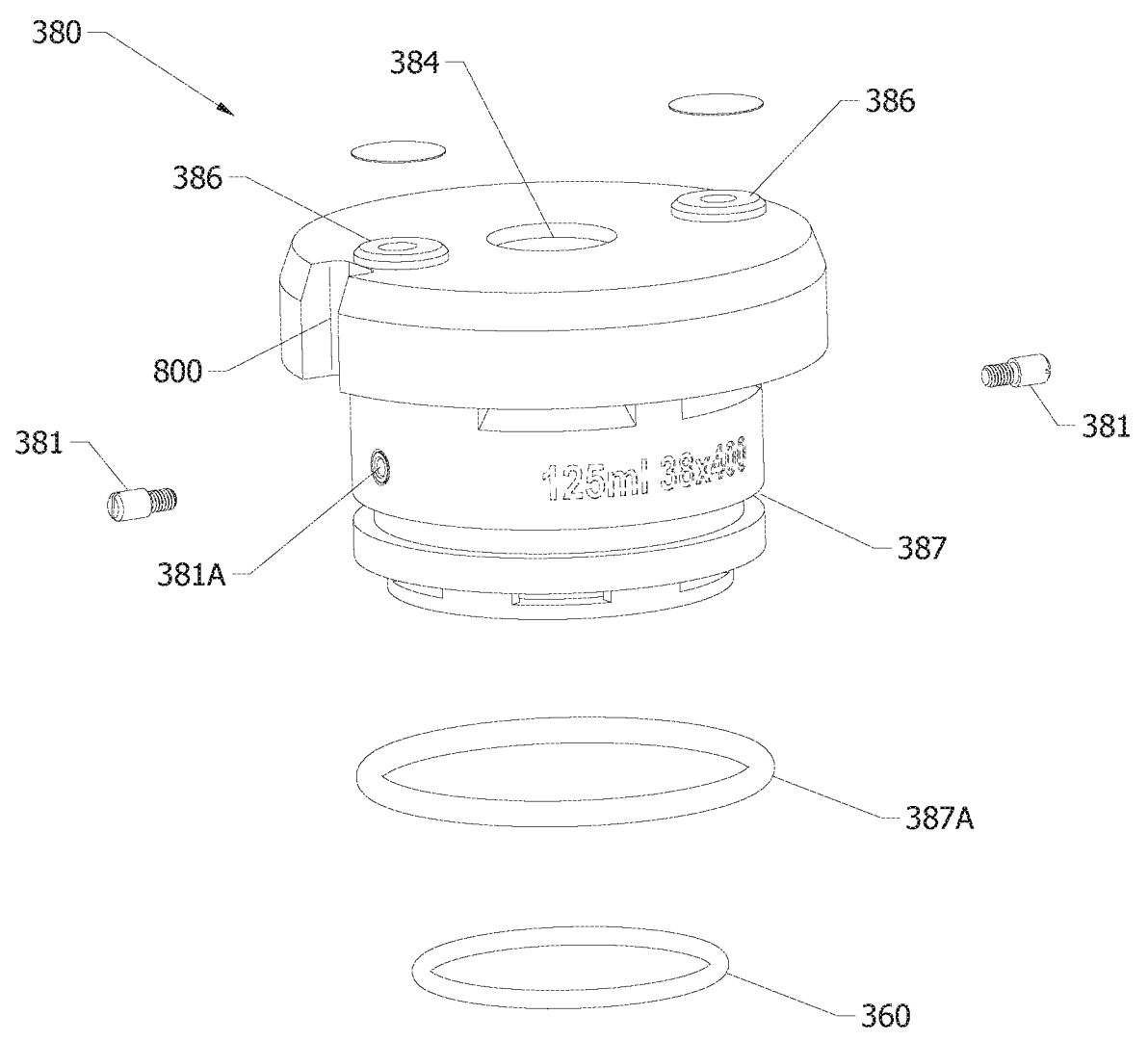
FIG. 22 is a front, perspective, exploded view of a sample bottle mounting structure that is positioned in the manifold.
Figure 23:
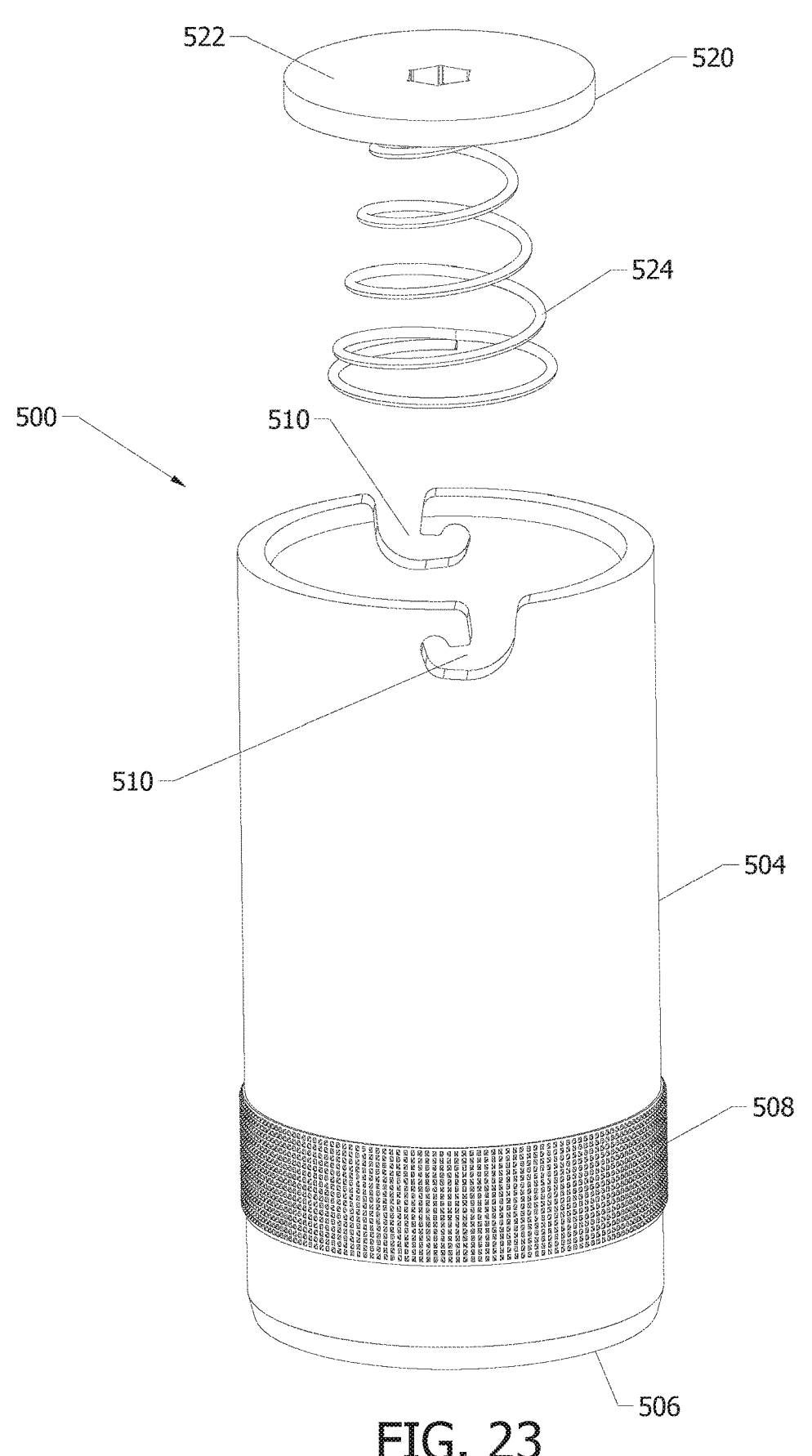
FIG. 23 is a front, perspective, exploded view of a protective container according to this disclosure.

As seen in FIG. 22, structure 380 has two top caps 386 that align it in manifold 300 and an opening 384 through which fluid from manifold 300 can pass when the valve is opened. An o-ring 387A fits into groove 387 to seal the opening of sample bottle 400 from the environment. Set screws 381 are received in openings 381A to help secure the structure 380.

Figure 30:
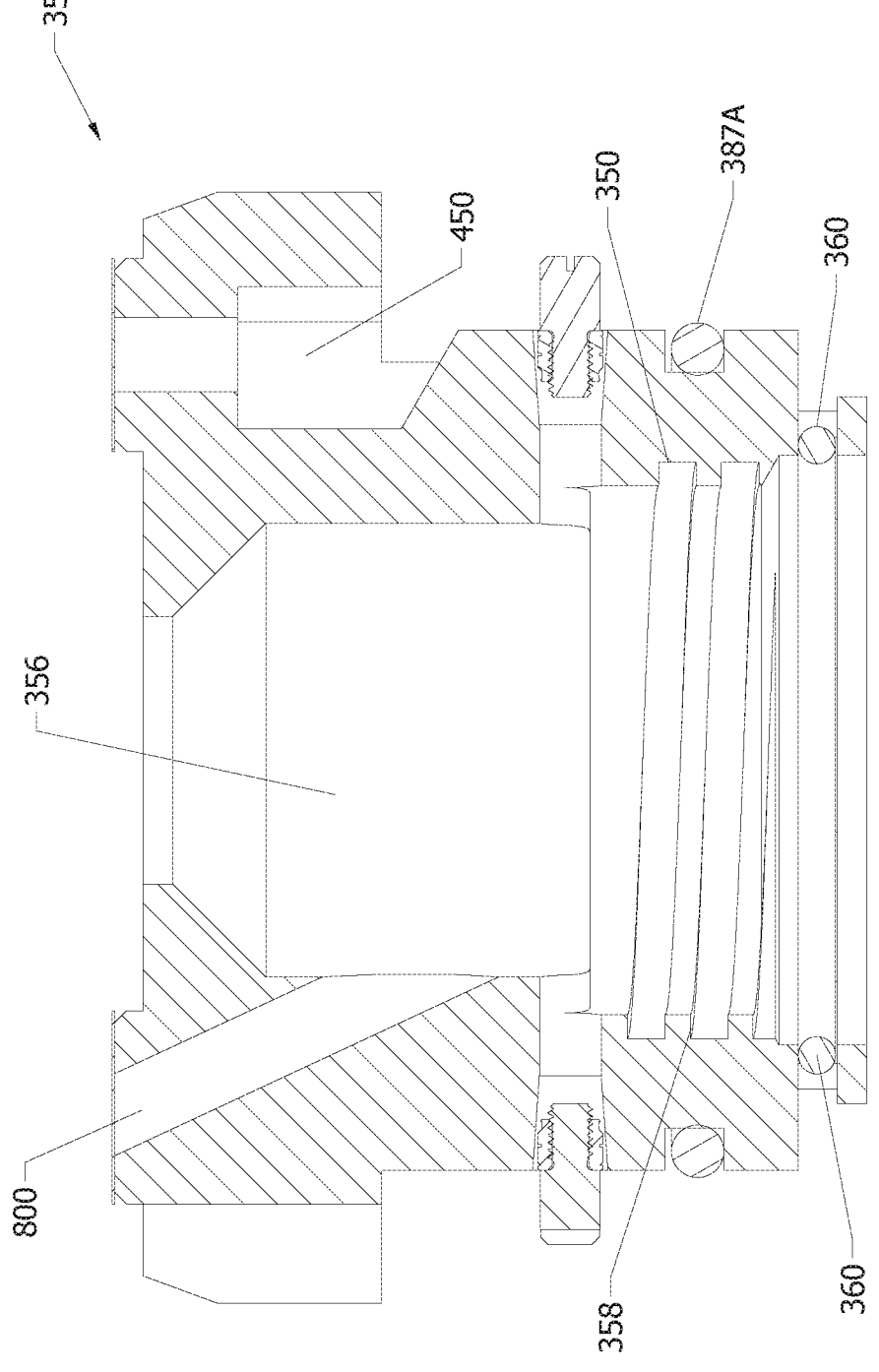
FIG. 30 is a side, cross-sectional view of a sample bottle mounting structure according to this disclosure.
Figure 31:
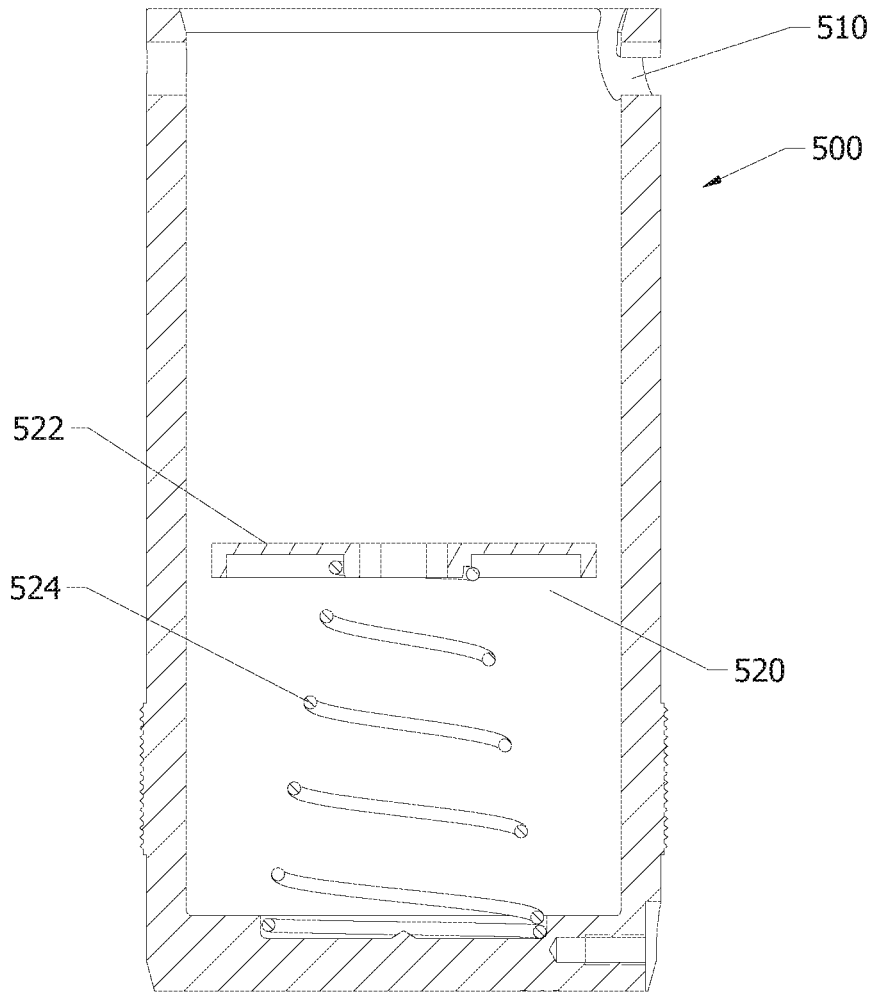
FIG. 31 is a side, cross-sectional view of the protective cannister of FIGS. 1 and 8.
Figure 32:
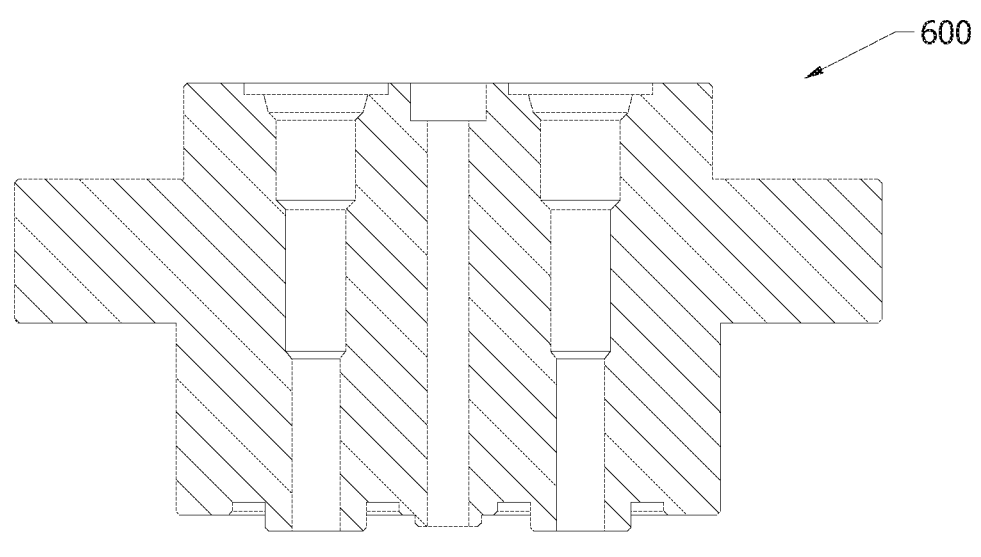
FIG. 32 is a top, cross-sectional view of a manifold block taken through line C-C of FIG. 5.
Figure 33:
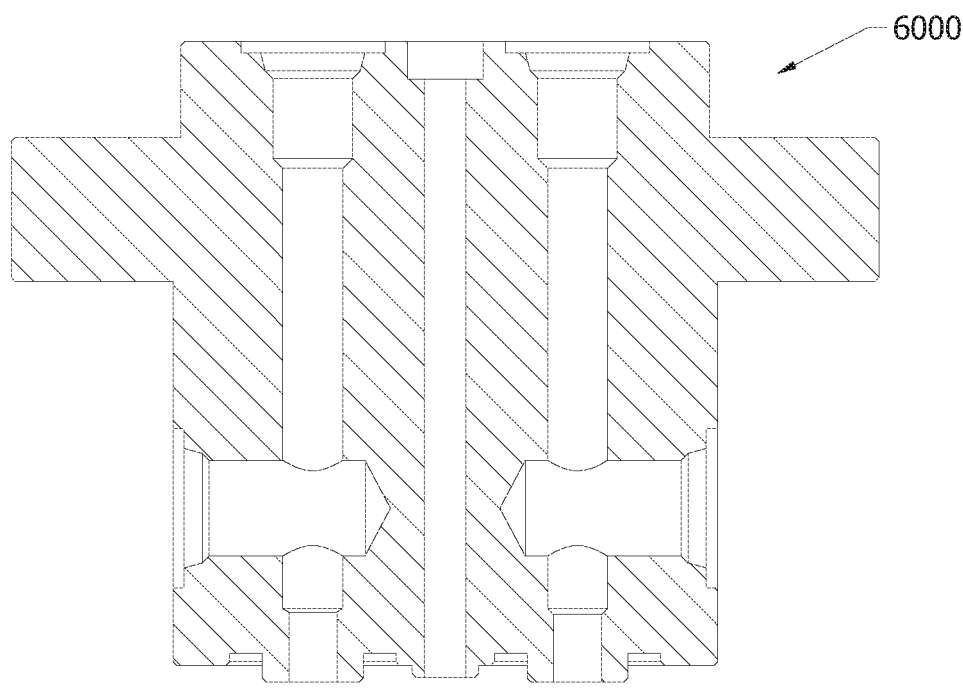
FIG. 33 is a top, cross-sectional view of a manifold block taken through line A-A of FIG. 6.
Figure 34:
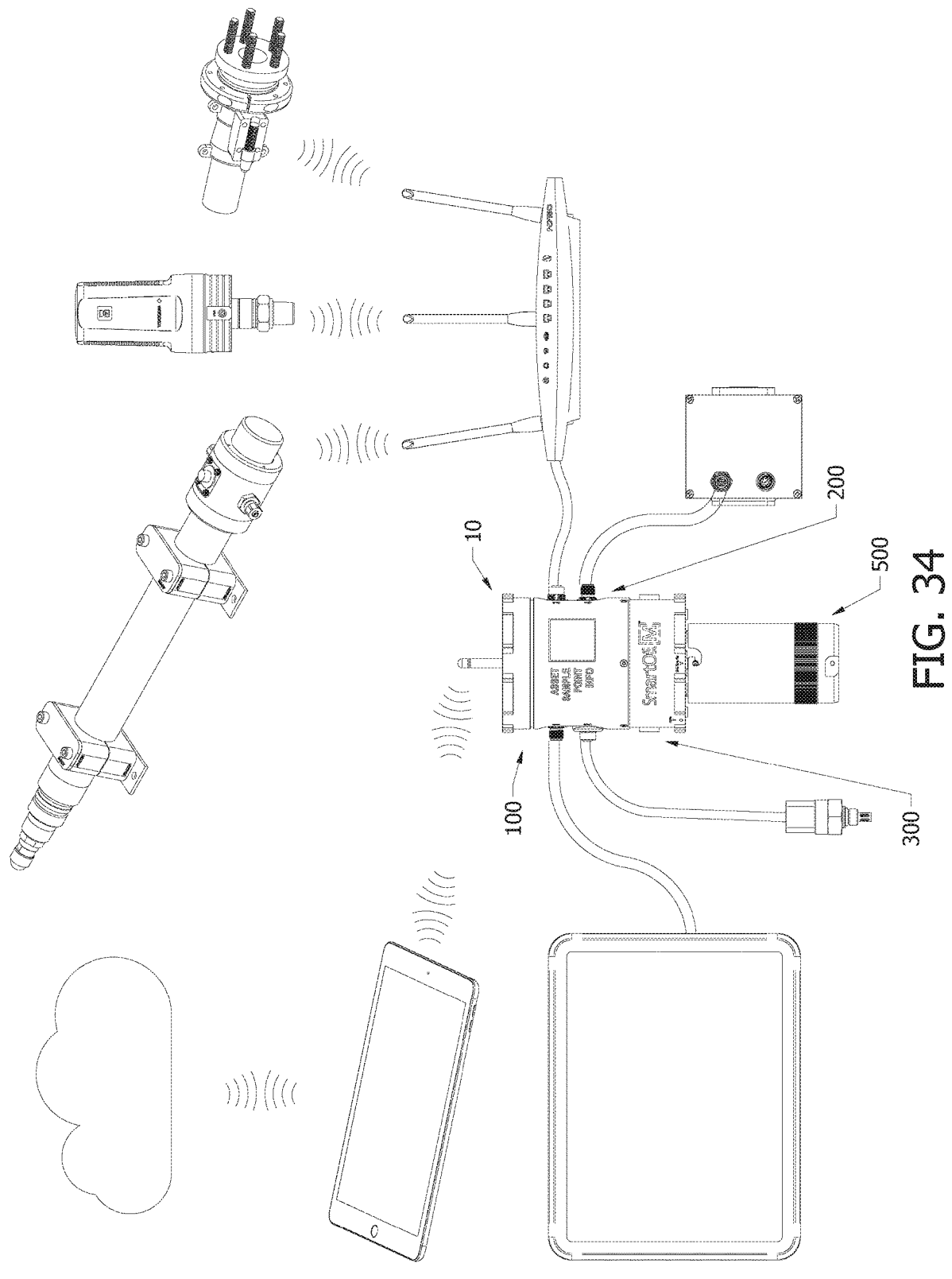
FIG. 34 is a front, partial perspective view illustrating an environment in which device 10 may function.
Figure 35:
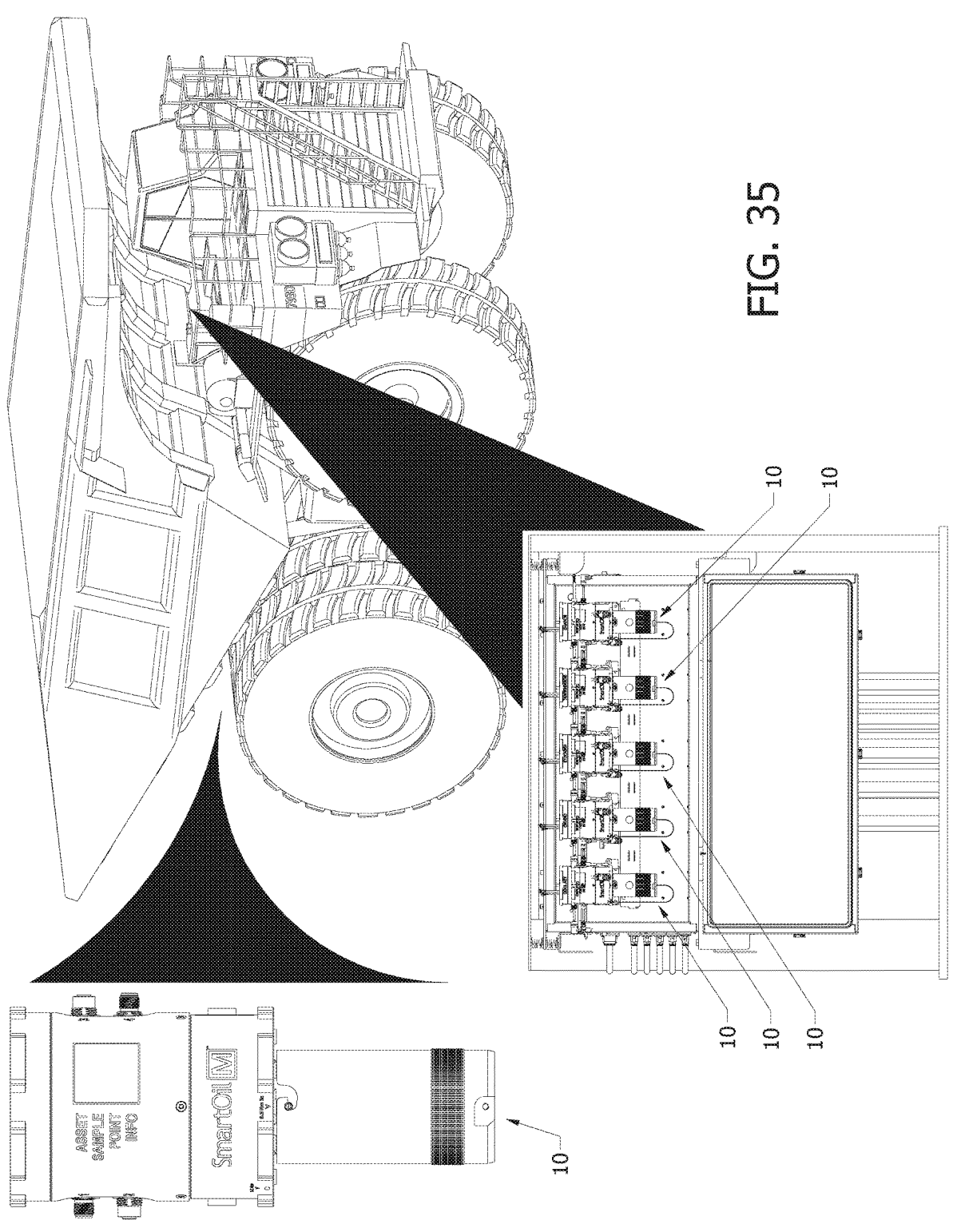
FIG. 35 illustrates a machine that includes multiple devices according to this disclosure, wherein each device may monitor a different fluid.

FIG. 30 is a close-up, cross-sectional view of structure 380.

Spacer Vent Passage

Figure 24:
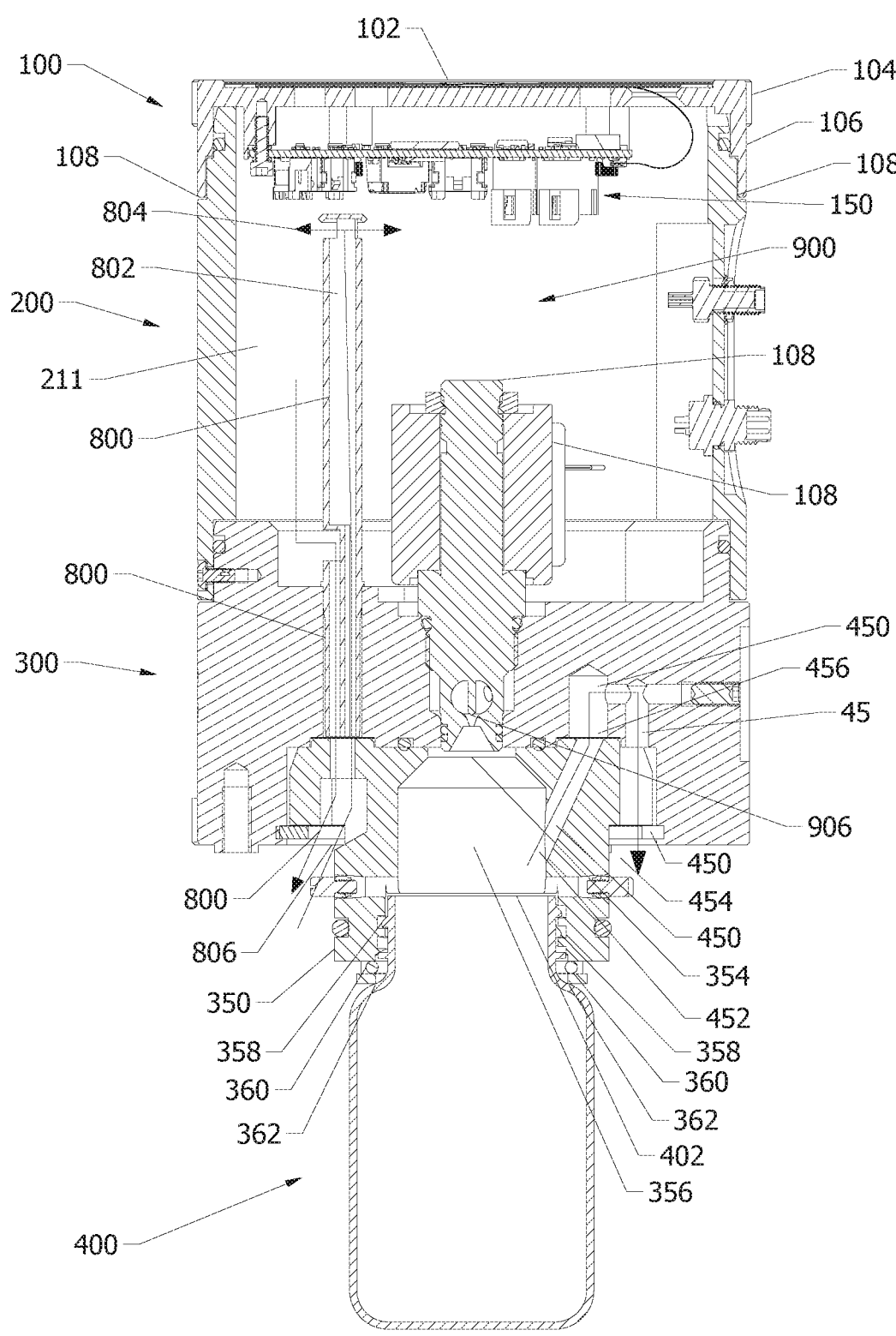
FIG. 24 is a front, cross-sectional view of the device of FIG. 1 without an external antenna or protective cannister.

A spacer vent passage 800, which is best seen in FIG. 24, passes from the spacer cavity 211, through the sample bottle mounting structure 380, to the outside of the device. The purpose of vent passage 800 is to equalize the pressure in cavity 211 with the atmospheric pressure outside of the device. Vent passage 800 includes a tube 802 that has an opening 804 inside of cavity 211 and an opening 806 to the outside in sample bottle mounting structure 380. A moisture barrier 808, which may be Gortex® fabric, is positioned in spacer vent passage 800 to help prevent moisture from the outside to enter cavity 211.

Sample Bottle Vent

When fluid is released into sample bottle 400, the air in sample bottle 400 must be vented. A bottle vent 450, shown in FIG. 24, permits such venting. Vent 450 has an opening 452 in the sample bottle mounting structure 380 at the opening 356 above sample bottle opening 402. Vent 450 has an exit opening 454 to the outside, and a moisture barrier 456, which may be Gortex® fabric, that helps prevent moisture from the outside air from entering sample bottle 400.

Valve Assembly

Figure 29:
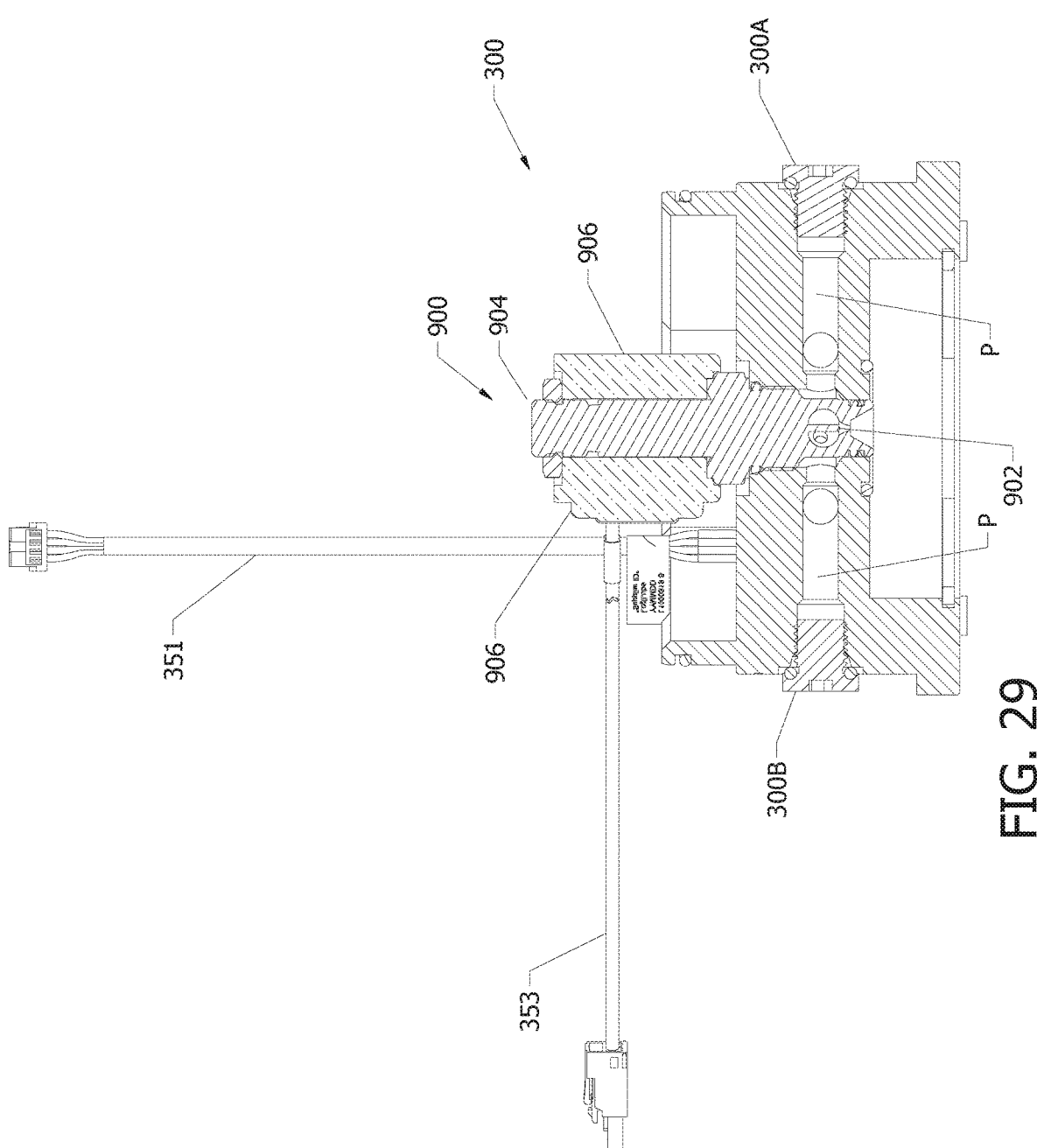
FIG. 29 is a side, cross-sectional view of the manifold of FIG. 1.

A valve assembly 900, best shown in FIGS. 24 and 29, includes a pin valve 902, a valve member 904, and a solenoid 906. The valve assembly 900 is in a closed position unless activated by PCBA 150. When activated, the valve assembly 900 moves to its open position and permits fluid from pathway P of the manifold 300 to move through space 356 and into sample bottle 400. The duration for valve assembly 900 to remain open depends on the type of fluid of which a sample is being taken, the amount of fluid required for the sample, the pressure of the fluid in pathway P, and the temperature of the fluid in pathway P. Each of these parameters is communicated to or programmed into PCBA 150, which opens valve assembly 900 for the correct amount of time.

Manifold Block

Figures 5, 6, 7:
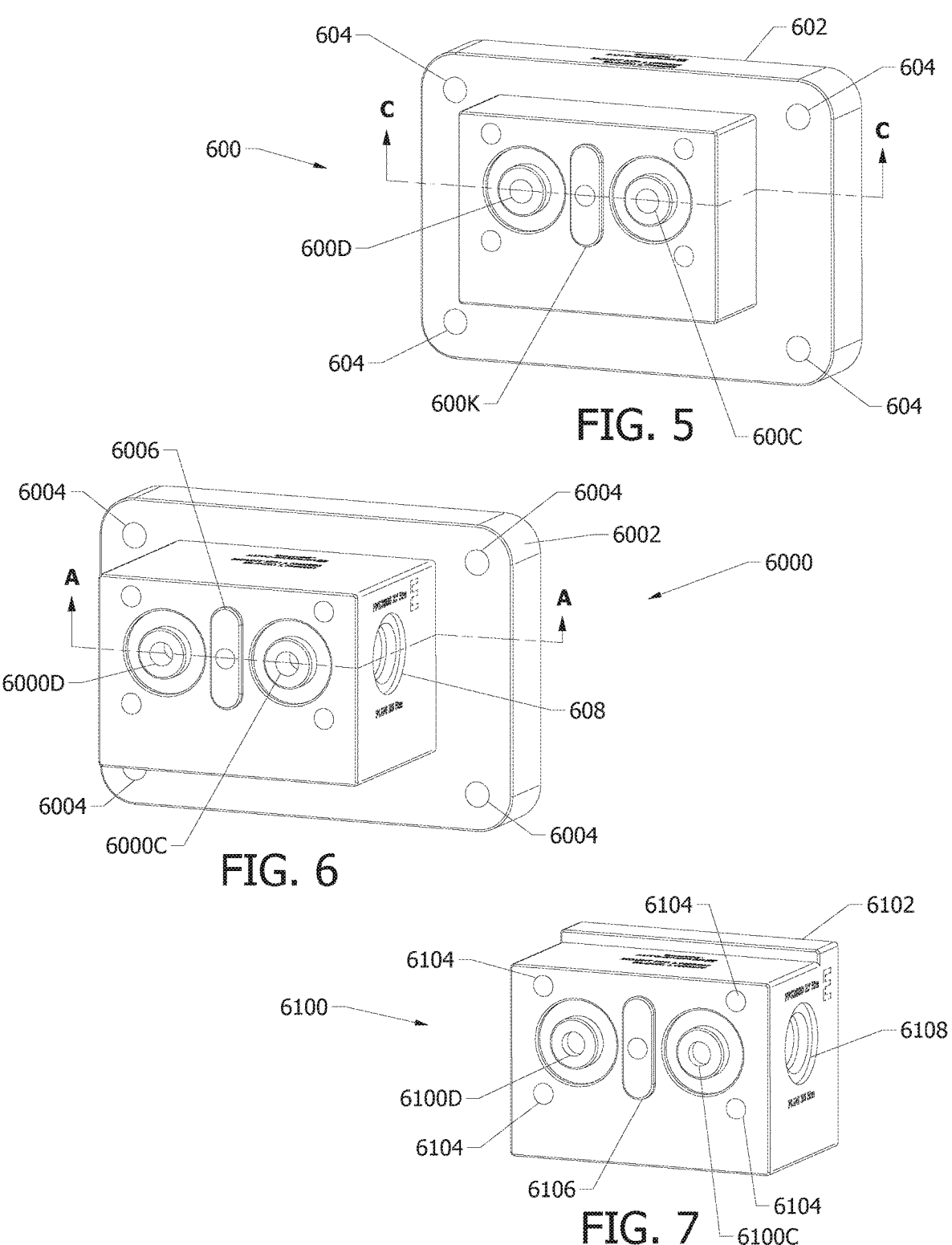
FIG. 5 is a side, perspective view of a manifold block according to this disclosure.
FIG. 6 is a side, perspective view of an alternative manifold block according to this disclosure.
FIG. 7 is a side, perspective view of an alternative manifold block according to this disclosure.
Figure 26:
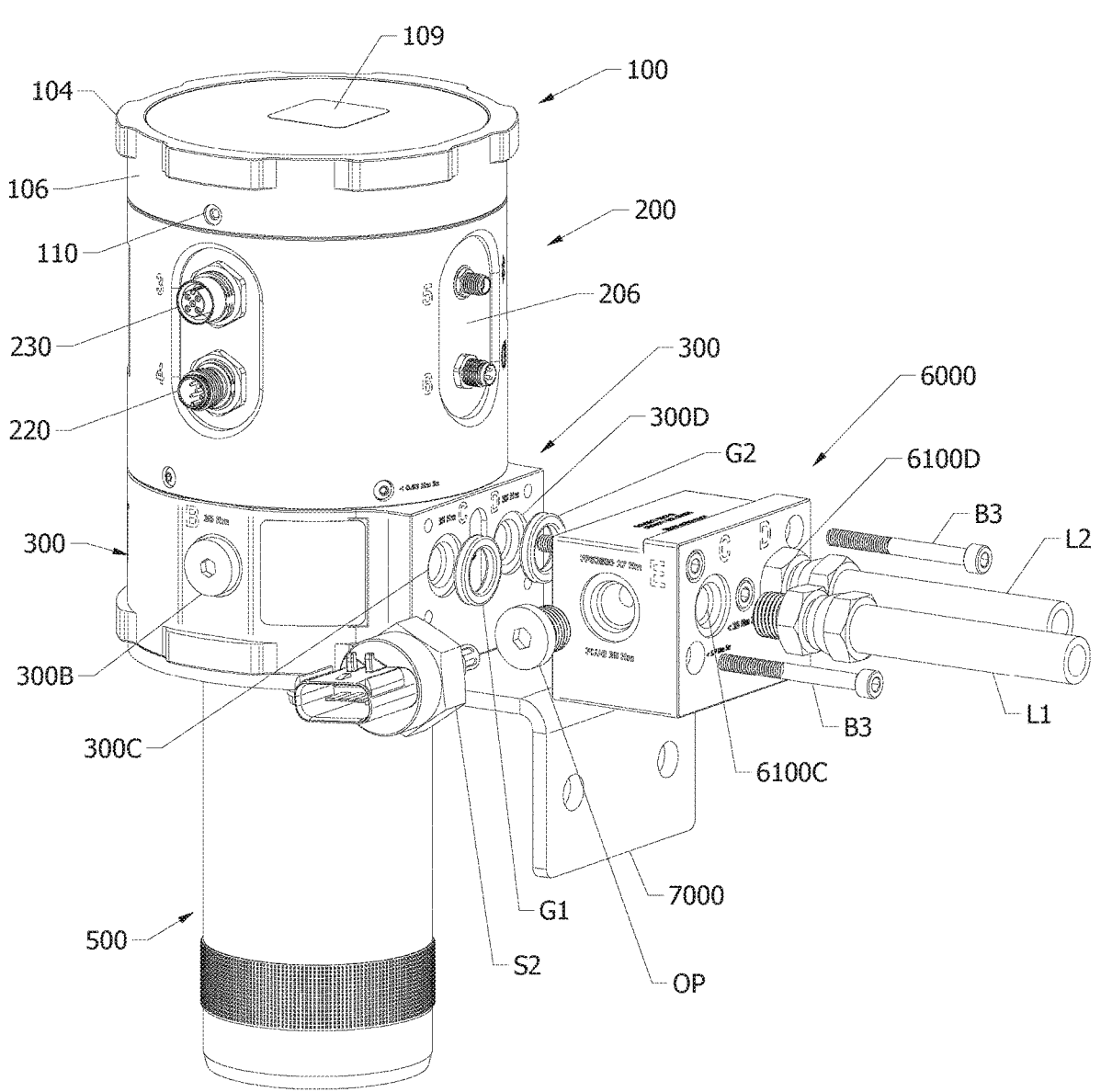
FIG. 26 is a side, perspective, partially exploded view of the device of FIG. 1 with a mounting bracket.

FIGS. 5-7, 25, and 26 show manifold blocks that can optionally be used with aspects of this disclosure. FIG. 5 shows a manifold block 600 that has a back plate 602, openings 604 configured to receive fasteners (not shown) to connect block 600 to manifold 300, as best seen in FIG. 26 (which includes manifold block 6100). Each of the manifold blocks 600, 6000, and 6100 or any other manifold block is preferably attached to manifold 300 in the same manner as shown in FIG. 26.

The purpose of a manifold block, if used, is to provide one or more fluid sensors. The fluid sensors could be of any type desired by a customer, such as any of the sensors mentioned herein.

Manifold block 600 further includes a fluid passage C and a fluid passage D that communicate, respectively, with passages PC and PD in manifold 300, as can be seen in FIG. 25 (which shows manifold 6000). Block 600 does not include sensors. Manifold block 600 also includes a raised key 600K that mates with a depression on manifold 300 to properly align the two structures.

Manifold block 6000, shown in FIG. 6 and in cross section in FIG. 25, has a back plate 6002 and openings 6004 that receive bolts B3 (shown in FIG. 26) to attach it to manifold 300. Manifold block 6000 includes passages 6000C and 6000D that align and communicate, respectively, with openings 300C and 300D in manifold 300, which can be seen in FIGS. 25 and 26. Manifold block 6000 also includes openings 6008, 6009 that communicate, respectively with manifold passages MPC and MPD, Sensors S1 and S2 can be received, respectively, in opening 6008 and 6009 in order to monitor a parameter of the fluid passing through manifold passages MPC and MPD. The sensor readings can be communicated to PCBA 150 in any suitable manner. Manifold 6000 also includes a raised key 6006 to properly align it with manifold 300.

Manifold block 6100, shown in FIG. 7, is the same as manifold 6000 except that it has different back plate 6102.

A bracket 7000 may be used to hold a manifold block and remainder of a device in position on a machine to which they are mounted.

Sample Bottle

Sample bottle (or container) 400 has a body and a top with an opening 402. The top of bottle 400 has threads that mate with threads on structure 380, so bottle 400 is screwed onto structure 380.

Protective Container

Two versions of a protective container (also called a protective cannister) are shown, although any suitable protective container may be utilized. Or, a protective container may not be used. The purpose of the protective container is to protect sample bottle 400.

Figures 8, 9, 10:
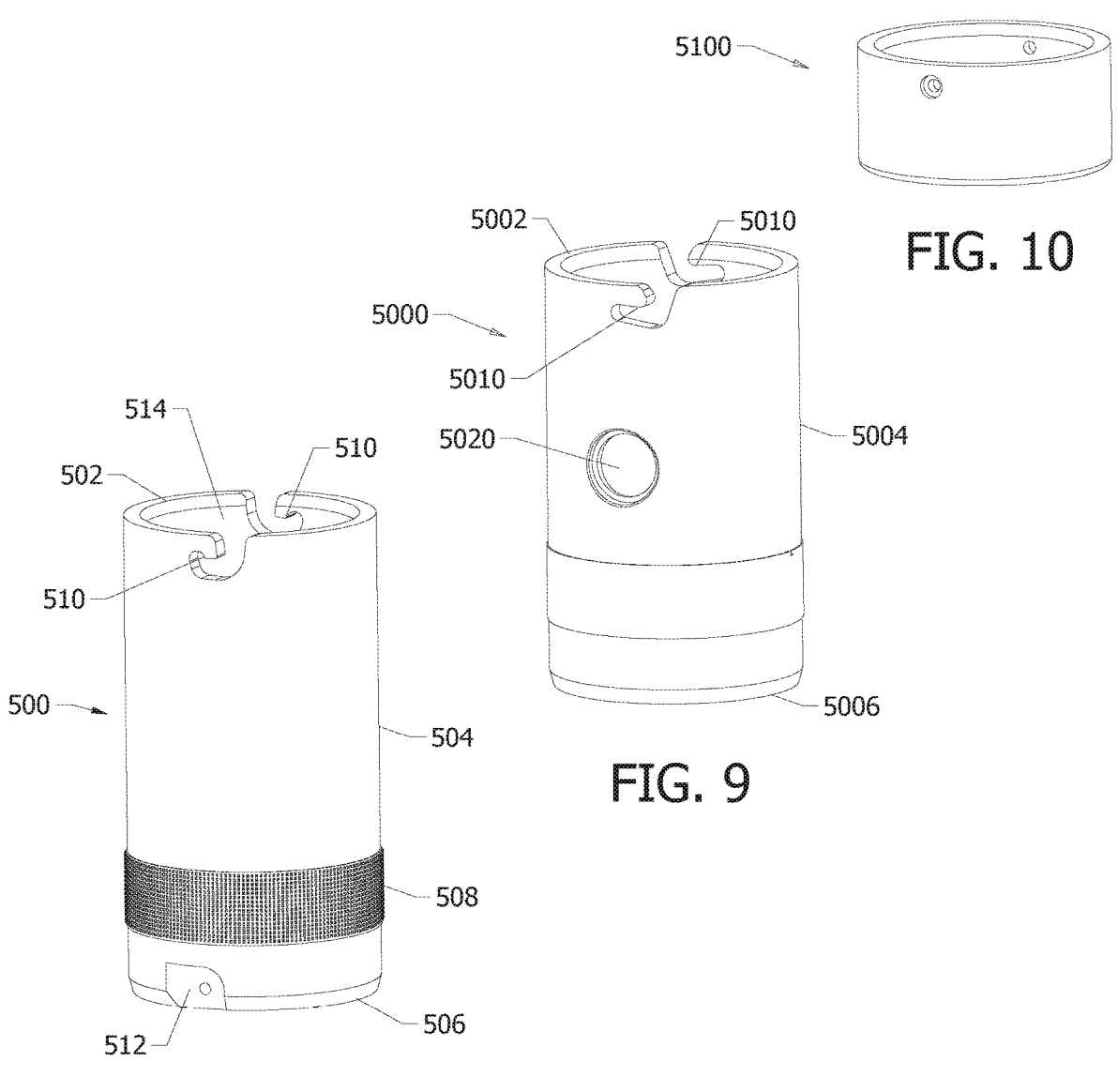
FIG. 8 is a front, perspective view of a protective canister according to this disclosure.
FIG. 9 is a front, perspective view of an alternative protective cannister according to this disclosure.
FIG. 10 is a front, perspective view of a sealing cap according to this disclosure.
Figure 11:
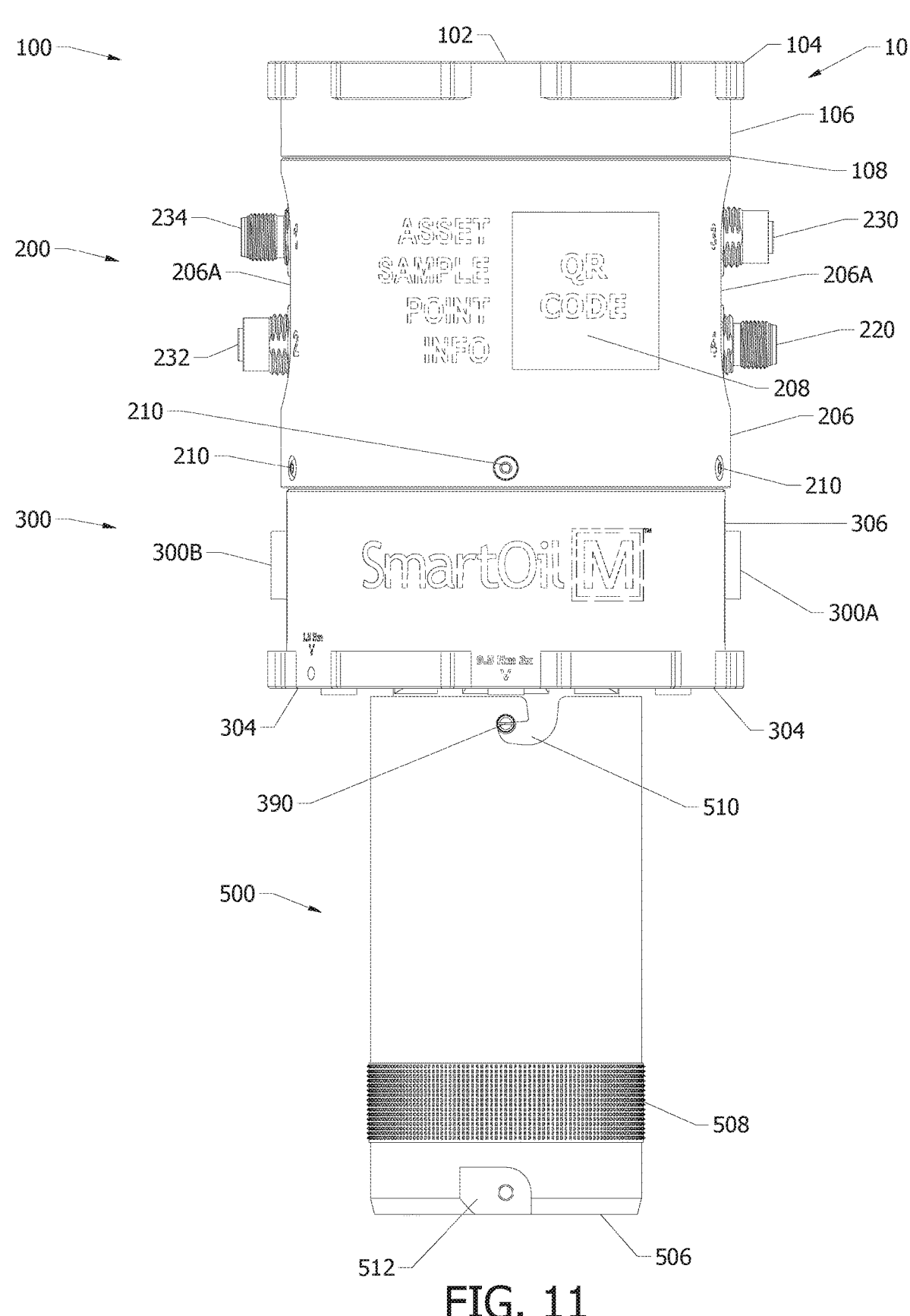
FIG. 11 is a front, assembled view of the device of FIG. 1 without an external antenna.

As shown in FIG. 8, protective container 500 is cylindrical and has an upper edge 502, an outer surface 504, a bottom 506, a grip surface 508, two locking openings 510, a structure 512, and a cavity 514. Cavity 514 is sized to receive and cover sample bottle 400 in order to protect it. Locking openings 510 receive fasteners 390 on structure 380 and are twisted to lock protective container 500 into place as shown in FIGS. 11 and 12, for example.

Protective container 5000, shown in FIG. 9, has the same structure and function as protective container 500 except that it has a transparent pane 520 through which the sample bottle 400 may be seen, does not have a grip surface.

Each of cannisters 500 and 5000 include a spring tension device comprising a disk 52o with a flat upper surface 522 and a spring 524. This device is positioned in the inside bottom surface of cannister 500 or 5000 to supply a pressure fit when the cannister 500 or 5000 is mounted over bottle 400 and secured to bolts 390.

Cap 5100, shown in FIG. 10, is used to cap the bottom of opening 356 when no sample bottle is used.

Some non-limiting examples of this disclosure follow:

Example 1: A device configured to measure one or more characteristics of a fluid, the device comprising a fluid intake port, a sensor in communication with the fluid to measure a parameter of the fluid, and a PCBA configured to store and/or transmit the measured parameter and/or send a command based on the measured parameter.

Example 2: The device of example 1 that further includes a sample bottle to retain a sample of the fluid.

Example 3: The device of example 1 that further includes a fluid output port.

Example 4: The device of example 1, wherein the input port is configured to connect to tubing, piping, or a reservoir that contains the fluid.

Example 5: The device of example 3, where in the output port is configured to connect to tubing, piping, or a reservoir that contains the fluid.

Example 6: The device of example 1 that includes a plurality of sensors and each of the plurality of sensors is configured to measure a different parameter of the fluid.

Example 7: The device of example 1 that includes a plurality of sensors and at least one of the plurality of sensors is configured to measure a different parameter of the fluid than the other of the plurality of sensors.

Example 8: The device of example 1, wherein the fluid is oil, transmission fluid, brake fluid, coolant, hydraulic fluid, grease, refrigerant, or fuel.

Example 9: The device of example 1 that is further configured to measure at least one parameter of a plurality of liquids.

Example 10: The device of any of examples 1-9, wherein the parameter is one or more of temperature, viscosity, pressure, total fluid level, particulate amount, and chemical parameters, and the amount of contaminants.

Example 11: The device of any of examples 1-10 that includes a plurality of PCBAs.

Example 12: The device of any of examples 1-11 that further includes a sample bottle configured to receive a sample of the fluid.

Example 13: The device of any of examples 1-12 that includes a thermistor and a pressure sensor.

Example 14: The device of example 13, wherein the thermistor and pressure sensor are on the PCBA.

Example 15: The device of example 1, wherein the sensor is on the PCBA.

Example 16: The device of example 1 that is configured to be mounted on an engine.

Example 17: The device of any of examples 1-16 that further includes a display configured to display one or more of the measured parameters.

Example 18: The device of any of examples 1-17 that further includes a PCBA configured to program the device.

Example 19: The device of any of examples 1-18 that further includes a transmitter configured to transmit at least one measured parameter.

Example 20: The device of any of examples 1-19, wherein the device can be programmed remotely through a wired or wireless connection.

Example 21: The device of any of examples 1-20 that is configured to constantly transmit the measured parameter.

Example 22: The device of any of examples 1-20 that is configured to transmit the measured parameter at predetermined time intervals.

Example 23: The device of any of examples 1-22 that is configured to transmit the measured parameter based on the geographical location of the device.

Example 24: The device of any of examples 1-23, wherein the PCBA has storage that stores the measured parameter.

Example 25: The device of example 24, wherein the PCBA stores a plurality of measured parameters of the fluid.

Example 26: The device of any of examples 21-23 or 25 that is configured to transmit a plurality of parameters of the fluid.

Example 27: The device of any of examples 1-26 that is further configured to receive information from one or more remote sensors.

Example 28: The device of example 27, wherein the PCBA is configured to receive the information wirelessly or through a wired connection.

Example 29: The device of example 27, wherein each remote sensor is connected to the PCBA by a wired connection.

Example 30: The device of example 24, wherein the storage is a RAM chip.

Example 31: The device of any of examples 27-29, wherein the information is the operation of a pump.

Example 32: The device of example 31, wherein the pump is an oil pump, coolant pump, or hydraulic pump or engine.

Example 33: The device of example 12, wherein the sample bottle is at the bottom of the device.

Example 34: The device of example 12 or 33, wherein the sample bottle is filled with a sample at pre-determined time intervals.

Example 35: The device of example 12 or 33, wherein the sample bottle is filled with a sample if the measured parameter meets a pre-determined threshold.

Example 36: The device of any of examples 1-35 that is configured to send an alarm is a pre-determined threshold is met.

Example 37: The device of any of examples 1-36 that is configured to transmit information by one or more of Wi-Fi, Bluetooth, and a cellular network.

Example 38: The device of any of examples 1-37 that further includes a cover.

Example 39: The device of example 38, wherein the PCBA is attached to the bottom of the cover.

Example 40: The device of any of the examples of 1-39 that further includes a solenoid that has (a) a first position in which the fluid cannot enter a sample bottle, and (b) a second position in which the fluid can enter the sample bottle.

Example 41: The device of example 40, wherein the solenoid is below the cover.

Example 42: The device of any of examples 1-41 that further includes a connector into which an external sensor connection can be plugged.

Example 43: The device of any of examples 1-42 that further includes a battery.

Example 44: The device of example 43, wherein the battery is rechargeable.

Example 45: The device of any of examples 1-44 that includes a sample bottle and a protective cannister that is outside of and retains the sample bottle.

Example 46: A system including any of the devices of examples 1-45 and a machine that includes at least one fluid having a parameter to be measured.

Example 47: The system of example 46 that includes a plurality of devices.

Example 48: A system according to any of examples 46-47 that includes a plurality of devices and each of the plurality of devices is configured to monitor the parameter of a different fluid.

Example 49: The system of any of examples 46-48, wherein the device is, or devices are, configured to be outside of the machine.

Example 50: The system of example 49, wherein the plurality of devices are at the same location on the machine.

Example 51: The system of example 49, wherein at least two of the plurality of devices are at the same location on the machine.

Some further non-limiting examples of the invention are as follows:

Example 1: A device for monitoring one or more fluids in a machine, the device comprising:

(a) one or more sensors that measure one or more of the temperature, volume, pressure, particulate level, liquid contaminant level, viscosity of one or more fluids, the amount of additives in the fluid, the amount of gas in the fluid, the level of oxidation of the fluid, and the amount of organic solids in the fluid.

(b) a PCBA that receives the one or more measured parameters and determines an action, wherein the action is to (i) do nothing, (ii) shut down the machine, (iii) limit the operating speed of the machine, (iv) send an alert to the machine operator, or (v) schedule machine maintenance.

Example 2: The device of example 1 that is mounted to the machine.

Example 3: The device of example 1 that further includes a fluid sample bottle.

Example 4: The device of example 1 that further includes a by-pass line that is in communication with the device and that is in communication with a main line of the fluid.

Example 5: The device of example 4, wherein the by-pass line includes a valve having a first position in which fluid from the main line does not enter the by-pass line and a second position in which fluid from the main line enters the by-pass line.

Example 6: The device of any of examples 1-5 that includes a fluid monitoring unit, a fluid sampling unit, and a PCBA.

Example 7: The device of any of examples 1-6, wherein the fluid is one or more of grease, oil, hydraulic fluid, engine coolant, air conditioning liquid, brake fluid, and window cleaning fluid.

Example 8: The device of any of examples 1-7 that includes one or more optical sensors configured to monitor one or more viscosity, pressure, temperature, density, dielectric constant, viscosity, water content, flow rate, fluid consumption rate, particulate amount, and particles shed from the machine.

Example 9: The device of any of examples 1-8, wherein the data sampling rate is 20 KHz or less.

Example 10: The device of any of examples 1-9 that further includes internet of things (IoT) enabled sensors in communication with the PCBA, wherein the IoT sensors monitor one or more of machine vibration, machine revolutions per minute (RPM), and torque.

Example 11: The device of any of examples 1-10, wherein the sensors are remote to the system.

Example 12: The device of any of examples 1-11 that is powered by AC or DC power.

Example 13: The device of any of examples 1-12 that is powered by the machine.

Example 14: The device of any of examples 1-13, wherein the PCBA receives information from a supervisory control and data acquisition (SCADA) system, wherein the SCADA information provides benchmarking against other machines within a fleet.

Example 15: The device of any of examples 1-14, wherein the data provided to the PCBA by the one or more sensors is time and date stamped.

Example 16: The device of any of examples 1-15 that further includes a central controller configured to receive information from the PCBA.

Example 17: The device of any of examples 1-16 that further includes a central controller remote to the machine and the PCBA is configured to communicate with the central controller.

Example 18: The device of example 17, wherein the PCBA communicates with the central server on 30-second intervals.

Example 19: The device of example 17 or 18, wherein the PCBA communicates wirelessly with the central server.

Example 20: The device of any of examples 17-19, wherein the central controller is configured to analyze data received from the PCBA.

Example 21: The device of example 20, wherein the central controller compares the data to one or more of the data received from one or more other operating machines, manufacturer specifications, and one or more machines that failed.

Example 22: The device of any of examples 17-21, wherein the central controller determines the remaining, useful life of the machine.

Example 23: The device of any of examples 17-22, wherein the central controller determines the time for the next maintenance of the machine.

Example 24: The device of any of examples 1-23 that further includes a display on the machine that displays one or more the measured parameters.

Example 25: The device of example 24 that displays the measured parameters in terms of a percentage change from target values.

Some further non-limiting examples of the disclosure follow:

Example 1: A device for measuring the parameters of a fluid, the device comprising:

(a) a first module comprising a PCBA;

(b) a second module connected to the first module and comprising one or more ports, wherein at least one of the one or more ports includes a connector connected to a remote sensor; and the at least one of the one or more ports is also connected to the PCBA.

Example 2: The device of example 1 that further comprises a third module connected to the second module, wherein the third module comprises a fluid input port configured for fluid to enter the third module, a fluid pathway, a fluid output port configured for fluid to exit the third module, and one or more sensors in the third module configured to measure one or more parameters of a fluid.

Example 3: The device of example 2 that further includes a sample container attached to the third module, wherein the sample bottle is configured to receive a sample of fluid that enters the third module.

Example 4: The device of example 3, wherein the sample bottle is threadingly attached to the third module.

Example 5: The device of any of examples 2-4, wherein the third module comprises a module sensor for determining fluid temperature, and a module sensor for determining fluid pressure.

Example 6: The device of any of examples 2-5, wherein the one or more module sensors are in communication with the PCBA.

Example 7: The device of any of examples 2-6, wherein the third module further includes a valve in communication with the fluid pathway, and the valve has a closed position and an open position in which fluid flows out of the valve.

Example 8: The device of example 7, wherein the sample container has an opening and the valve is above the opening and fluid flows past the opening and into the sample bottle when the valve is in its open position.

Example 9: The device of example 7 or 8, wherein the valve is moved from its closed position to its open position by a signal received from the PCBA.

Example 10: The device of example 9, wherein the valve is moved to its open position for a time period that is determined by (a) the temperature of the fluid, (b) the pressure of the fluid, and (c) the volume of the fluid sample to be placed in the sample bottle.

Example 11: The device of any of examples 7-10, wherein the valve includes a pin valve connected to a valve assembly.

Example 12: The device of example 11, wherein the valve assembly is positioned partially in the third module and partially in the second module.

Example 13: The device of any of examples 1-12, wherein the second module further includes a power connection having an inner side connected to a wire that transmits power to the PCBA and an outer side configured to be connected to a power source.

Example 14: The device of any of examples 1-13 that operates on D.C. power.

Example 15: The device of example 13, wherein the outer side is connected to a power source.

Example 16: The device of any of examples 1-15 that is mounted on a vehicle.

Example 17: The device of any of examples 13-15, wherein a machine to which the device is mounted provides the power source.

Example 18: The device of any of examples 1-13, wherein the fluid is engine oil, hydraulic fluid, brake fluid, steering fluid, engine coolant, cleaning fluid, grease, kerosene, or gasoline.

Example 19: The device of any of examples 3-18 that further includes a protective container surrounding the sample bottle.

Example 20: The device of example 19, wherein the protective container is attached to the third module.

Example 21: The device of any of examples 3-18, wherein the third module includes an air venting passage configured to allow air to vent from the sample bottle, through the air venting passage and to the outside of the third module when fluid enters the sample container.

Example 22: The device of example 21 that includes a moisture barrier in the air venting passage.

Example 23: The device of example 21, wherein the moisture barrier is comprised of Gortex® fabric.

Example 24: The device of any of examples 21-23, wherein the air venting passage has an outlet at a bottom surface of the third module.

Example 25: The device of any of examples 3-24, wherein the third module further includes an open space between the valve and the sample bottle.

Example 26: The device of any of examples 1-25, wherein the second module further includes a connector configured to connect to a wireless signal receiver.

Example 27: The device of example 26, wherein the connector is configured to receive a Bluetooth signal.

Example 28: The device of any of examples 1-27, wherein the PCBA is configured to communicate with a central controller remote to the device.

Example 29: The device of any of examples 1-28, wherein the modules are integrally formed as a single piece.

Example 30: The device of any of examples 1-28, wherein the modules are separate pieces that are connected.

Example 31: The device of any of examples 1-28, wherein the first module and second module are integrally formed.

Example 32: The device of any of examples 2-28, wherein the second module and third module are integrally formed.

Example 33: The device of any of examples 1-32 that further includes a manifold block connected to the second module.

Example 34: The device of any of examples 1-32, wherein the second module includes one or more sensor connectors.

Example 35: The device of example 34 that further includes one or more sensors attached to the device.

Example 36: The device of example 34, wherein one or more sensors are integrally formed with the device.

Example 37: The device of any of examples 3-36, wherein the sample bottle is comprised of plastic.

Example 38: The device of any of examples 19-37, wherein the protective cannister is comprised of aluminum.

Example 39: The device of any of examples 1-38 that includes a particle sensor.

Example 40: The device of any of examples 3-39, wherein the sample bottle is filled by the valve being moved to its open position.

Example 41: The device of example 40, wherein the PCBA moves the valve to its open position for a time based on (a) measured fluid temperature, (b) measured fluid pressure, and (c) the volume of liquid required for the sample.

Example 42: The device of any of examples 1-41 that is connected to a fluid flow line of a machine.

Example 43: The device of example 42, wherein the fluid flow line is a bypass line from a main fluid flow line.

Example 44: A machine including a main fluid flow line, a bypass fluid flow line, and the device of any of examples 1-43 connected to the bypass fluid flow line.

Example 45: The machine of example 44 that is a vehicle.

Example 46: The machine of example 45 that is a truck.

Example 47: The device of any of examples 1-43 that further comprises a dielectric constant sensor.

Example 48: The device of any of examples 1-43 or 47 that further comprises a capacitance sensor.

Example 49: The device of any of examples 1-43 or 47-48 that further includes an oil additive sensor.

Example 50: The device of any of examples 1-43 or 47-49 that further includes an oil additive basin in communication with an oil reservoir, and the processor commands a pump to move additive from the basin to the reservoir, when the measured level of oil additive reaches a predetermined amount.

Example 51: The device of any of examples 1-43 or 47-50 that further includes one or more vibration sensors.

Example 52: The device of example 51, wherein the vibration sensor is on a motor shaft, a motor, and/or a valve cover.

Example 53: The device of any of examples 1-43 or 47-52 that has a maximum outer diameter of 4.5".

Example 54: The device of any of examples 1-53 that has between one and six sensor ports.

Example 55: The device of any of examples 1-43 or 47-53, wherein the processor has software that can be remotely modified or updated.

Example 56: The device of any of examples 1-43 or 47-55 that further includes a battery to operate the device when no power is received from the power source.

Example 57: The machine of examples 44-46 that includes a plurality of devices.

Example 58: The device of any of examples 1-43 or 47-56 that further includes a QR code.

Example 59: The device of any of examples 1-43, 48-56 or 58, wherein the second module has a cavity is vented to the outside to equalize the pressure in the cavity to the atmospheric pressure.

Example 60: The device of example 59, wherein the second module is vented through a ventilation path that includes a moisture barrier.

Example 61: The device of example 60, wherein the moisture barrier is Gortex® fabric.

Example 62: The device of any of examples 59-61, wherein the second module includes an air vent.

Example 63: The device of any of examples 3-43, 48-56, or 58-62, wherein the fluid sample is 100 ml.

Some further non-limiting examples of this disclosure are as follows:

Example 1: Rotating machine with real-time monitoring of grease fluid condition and sampling based on periodic interval or exception:

(a) parameters monitored by the system include: viscosity, temperature, pressure, density, die-electric constant, water content, flow rate, consumption rate, as well as wear particles shed off the points where the rotating machine has contact such as the gear lobes in a gearbox or a bearing raceway;

(b) dynamic configuration of triggers for exception samples based on asset operational history or comparison with fleet performance; and (c) providing validation of fluid flushing/machine servicing procedures by detecting whether or not residual additive constituent components detected prior to the fluid change remain in high concentration after the fluid change.

Example 2: Determination of remaining useful life of grease fluid using algorithms which take into account operational parameters (a) fluid type may be lubricating oil, hydraulic fluid or coolant at is used m conjunction with the rotating machine;

(b) algorithms to determine remaining useful life of grease and/or fluid are part of an edge computing system;

(c) validation of remaining useful life model (determined by edge processing algorithms or server based algorithms) vs. empirical measurement of monitored parameters; and (d) Computation of fleet-wide asset performance degradation mot e (s).

Example 3: Early warning signs of potential degradation that can be monitored by the unit and used to determine a course of action such as asset control or grease and/or fluid change-out:

(a) desiccant filter monitoring;

(b) determination of electrolysis potential; and (c) foaming detection.

Example 4: Use of monitored parameters for asset control:

(a) De-rating (throttling back) power based on exception sample;

(b) De-rating/curtailment interval lasts until lab results corroborate real-time sensor data (e.g., up to 2 days for example);

(c) Controlling ramp rate of torque/speed curve (e.g., regulating asset operating RPM) during cold start or hot re-start;

(d) Reducing the ramp rate if monitored parameter (e.g., particle count, water content, viscosity, etc.) is above threshold level (e.g., "easing" unit into normal operating conditions); and (e) Comparison of assets across fleet (e.g., same model number in comparable operating environment);

(f) Integration of sensor data for ambient condition monitoring (e.g., cold weather stati);

(g) Up-rating (throttling up) power based on lower consumption life for grease and/or fluid remaining useful life or component remaining useful life vs. comparable fleet assets;

(h) Re-evaluation of remammg useful life threshold/alteration of condemning limit (i) Preventative life extension asset control based on pre-cursor (e.g., system detects possible foaming & de-rates until sample can be evaluated) Relates to 4a above.

(j) Algorithms could suggest specific additives depending on operational hours/component lifetime to enhance preservation of components (e.g., life extension to next scheduled maintenance window)

(k) Dynamically setting threshold levels for alerts which trigger exception samples based on fleet performance or asset characterization gearbox wear-in rate could result in lower threshold today vs. 10 years ago)

i. Dynamically re-evaluating condemning limits based on operational performance and comparison to flee-wide performance (l) Dynamically setting automatic sampling interval based on historical asset performance (e.g., sampling interval of 3 months could be extended or contracted depending on trends in data monitoring—vector analysis)

(m) Automatic sampling rate/period determined based on frequency/severity of exception samples (e.g., algorithms determine that based on past operational performance, the gearbox is "high risk" according to the system algorithms, so for next 6 months, samples will be taken monthly until monitored behavior changes)

(n) Net present value calculation of asset life consumption (e.g., grease and/or fluid remaining useful life could be a determinant of overall machine remaining useful life. The impact on the operational profile of the asset based on how "hard" it is being run, including the number and duration of de-rates and up-rates to output power, will have an impact on power plant performance)

(o) Predictive maintenance scheduling using remaining useful life of grease and/or fluid as well as remaining useful life estimation of components i. Calculation of optimal downtime period for fluid change (comparison with SCADA data)

Example 5: Co-location of spectrometer to evaluate samples (a) Real-time asset control based on spectrometer collaboration of grease and/or fluid degradation measurement (b) Continuous flow monitoring or periodic siphoning from main fluid flow conduit i. Process for discarding samples (or otherwise filtering and recycling fluid that has not degraded)

Some further non-limiting examples of this disclosure are as follows:

Example 1: A method for monitoring the characteristics of a fluid used to operate a machine while the machine is operating, the method comprising the following steps:

(a) separating a sample of fluid from a fluid used to operate the machine; and (b) testing the sample to determine one or more of temperature, viscosity, chemical composition, and particulate level, or instead (c) testing a sample of the fluid as it passes a sensor.

Example 2: The method of example 1, wherein the level of particulate sand particles is measured.

Example 3: The method of example 1, wherein the fluid is selected from one or more of the groups consisting of oil, brake fluid, coolant, transmission fluid, fuel, refrigerant, and hydraulic fluid.

Example 4: The method of example 1, wherein the sample size is 100 ml.

Example 5: The method of example 1, wherein the machine is a vehicle that has an engine.

Example 6: The method of example 5, wherein the vehicle further includes one or more of a braking system, a transmission, a fuel line, a coolant system, a refrigeration system, and a hydraulics system.

Example 7: The method of example 6, wherein if a sample is taken, the sample is separated and stored in a sample bottle.

Example 8: The method of example 7, wherein if a sample is taken, the sample is stored on the exterior of the machine.

Example 9: The method of example 8, wherein the sample is stored in a fluid bottle on the exterior of the machine.

Example 10: The method of any of examples 1-10, wherein each sample is collected at a predetermined time interval.

Example 11: The method of example 10, wherein the time interval is between 1-12 hours.

Example 12: The method of example 1, wherein the temperature of the fluid is constantly monitored.

Example 13: The method of example 1, wherein the pressure of the fluid is constantly monitored.

Example 14: The method of example 1, wherein the amount of total fluid in the machine is constantly monitored.

Example 15: The method of any of examples 2-14, wherein one or more of the temperature, pressure, and amount of total fluid is communicated to an operator.

Example 16: The method of example 15, wherein the communication is sent via a wired or wireless connection.

Example 17: The method of example 15 or 16, wherein the communication is received and displayed to an operator of the machine.

Example 18: The method of example 15, 16, or 17, wherein the communication is sent to a person or device remote from the machine.

Example 19: The method of any of examples 1-18 that further includes the step of adding a monitoring device that is in communication with a flow line or reservoir that contains the fluid.

Example 20: The method of example 19, wherein the monitoring device includes a cannister in which the sample is retained.

Example 21: The method of example 1 that further includes the step of adding a secondary flow line to a flow line or reservoir that contains the fluid.

Example 22: The method of example 21 that further includes the step of adding a monitoring device in communication with the secondary flow line.

Example 23: The method of example 22, wherein the monitoring device includes a cannister for retaining the sample.

Example 24: The method of example 18, 20, 22 or 23, wherein the monitoring device is in communication with a secondary flow line, a flow line, or a reservoir of the liquid.

Example 25: The method of example 1 that further includes one or more of the following steps:
  (a) turning the machine off if a pre-determined condition is met;
  (b) altering the function of the machine if a predetermined condition is met; and
  (c) sending an alert if a predetermined condition is met.

Example 26: The method of example 25, wherein the predetermined condition is one or more of:
  (d) a temperature,
  (e) a pressure,
  (f) a particulate level,
  (g) a viscosity,
  (h) a total fluid amount, and
  (i) a flow rate.

Example 27: The method of any of examples 1-26 that further includes monitoring the characteristics of a plurality of fluids.

Example 28: The method of any of examples 1-27 that further includes receiving commands from one or more of: an operator of the machine, a person not operating the machine, or a computing device.

Example 29: The method of example 28, wherein the command does one or more of the following: alters the function of the machine, inquires for another sample testing, inquires for a sample testing of an alternate fluid, turns off the machine, or sends a message to the machine operator.

Example 30: The method of example 27, wherein the characteristics of each of the plurality of fluids is determined by a separate monitoring device.

Example 31: The method of any of examples 1-30 wherein additional data about the operation of the machine is received from a remote sensor.

Some non-limiting examples of this disclosure are as follows:

Example 1: A device mounted to a machine for monitoring one or more fluid parameters of the machine, wherein the device comprises:
  (a) a printed circuit board assembly (PCBA);
  (b) a spacer that includes a power connector having a first end configured to be connected to an external power source, and a second end, and
  (c) a wire having a first end connected to the second end of the power connector and a second end connected to the PCBA.

Example 2: The device of example 1, wherein the PCBA is positioned at least partially in a cover that is attached to the spacer.

Example 3: The device of example 2, wherein the spacer has a top and a bottom and the cover is attached to the top of the spacer.

Example 4: The device of any of examples 1-3, wherein the spacer includes a cavity and the PCBA is positioned partially in the spacer cavity.

Example 5: The device of any of examples 2-4, wherein the cover and spacer are integrally formed.

Example 6: The device of any of examples 2-4, wherein the cover and spacer are separate components.

Example 7: The device of example 6, wherein the spacer has a top lip and a keyway in the top lip, and the cover has a projection configured to fit into the keyway so as to properly align the cover on the spacer.

Example 8: The device of example 6 or 7, wherein the top lip of the spacer further comprises a groove and an o-ring received in the groove, wherein the o-ring has a thickness sufficient for it to extend outside of the groove.

Example 9: The device of example 8, wherein the cover has an inner annular surface that presses against the o-ring when the cover is attached to the spacer in order to create a seal to help prevent particles and moisture from entering the spacer cavity or contacting the PCBA.

Example 10: The device of any of examples 1-9, wherein the spacer further includes one or more sensor connectors, wherein each sensor connector is configured to connect to a sensor.

Example 11: The device of example 10, wherein each sensor connector is configured to be connected to a sensor by a wire.

Example 12: The device of example 10 or 11, wherein each sensor connector that is connected to a sensor further includes a wired connection to the PCBA.

Example 13: The device of any of examples 10-12 that further includes one or more sensors.

Example 14: The device of example 13, wherein all of the one or more sensors are remote to the device.

Example 15: The device of example 13, wherein at least some of the one or more sensors are remote to the device.

Example 16: The device of example 13 or 15, wherein at least some of the one or more sensors are located on or in the device.

Example 17: The device of example 13, wherein all of the one or more sensors are located on or in the device.

Example 18: The device of any of examples 13-17, wherein the one or more sensors measure one or more of the following fluid parameters: temperature, viscosity, pressure, density, dielectric constant, water content, flow rate, consumption rate, total volume, total acid number (TAN), total base number (TBN), oxidation numbers, nitration levels, oil SAE grade, amount of wear particles, and contamination particles.

Example 19: The device of any of examples 1-18, wherein the machine is selected from the group consisting of a: truck, car, front-end loader, bulldozer, ship, airplane, windmill, grist mill, solar tracker, engine, and crane.

Example 20: The device of any of examples 1-19, wherein the spacer further includes an external antenna mount.

Example 21: The device of example 20 that further includes an antenna mounted to the external antenna mount, wherein the antenna is in wired or wireless communication with the PCBA.

Example 22: The device of any of examples 1-21, wherein the spacer is comprised of metal or plastic.

Example 23: The device of any of examples 2-22, wherein the cover is comprised of metal or plastic.

Example 24: The device of example 22, wherein the spacer is comprised of aluminum.

Example 25: The device of example 23, wherein the cover is comprised of aluminum.

Example 26: The device of any of examples 13-25, wherein the one or more sensors measure one or more of machine vibration, revolutions per minute (RPM), or torque.

Example 27: The device of any of examples 13-26, wherein the one or more sensors comprise optical sensor(s) and/or internet-of-things sensor(s).

Example 28: The device of any of examples 1-27, wherein the spacer has a first end connected to the cover and a second end connected to a manifold.

Example 29: The device of example 28, wherein the spacer and manifold are integrally formed.

Example 30: The device of example 28, wherein the spacer and manifold are separate components.

Example 31: The device of example 28 or 30, wherein the manifold has a first end a second end, and the first end has an upper lip comprising a groove with an o-ring positioned in the groove, wherein the o-ring has a thickness sufficient for it to extend beyond the groove.

Example 32: The device of example 31, wherein the second end of the spacer has an inner, annular surface, and the second end of the spacer is connected to the first end of the manifold and the inner, annular surface compresses the o-ring to create a seal that helps keep particles and moisture out of the inner cavity of the spacer and out of an interior of the manifold.

Example 33: The device of any of examples 28-32, wherein the manifold further comprises a fluid intake port, a fluid exit port, and a fluid pathway between the fluid intake port and the fluid exit port.

Example 34: The device of example 33, wherein the manifold further comprises a fluid temperature sensor located at one or more of the fluid intake port, the fluid pathway, and the fluid exit port.

Example 35: The device of example 33 or 34, wherein the manifold further comprises a fluid pressure sensor located at one or more of the fluid intake port, the fluid pathway, and the fluid exit port.

Example 36: The device of example 34 or 35, wherein each sensor is in communication with the PCBA by a wired or wireless connection.

Example 37: The device of any of examples 33-36, wherein the manifold includes a second fluid intake port, a second fluid exit port, and a second fluid pathway between the second fluid intake port and the second fluid exit port, wherein the second fluid pathway is connected to the fluid pathway.

Example 38: The device of example 37, wherein two of the fluid intake port, fluid exit port, second fluid intake port, and second fluid exit port are plugged.

Example 39: The device of any of examples 28-38 that further includes a manifold block connected to the manifold.

Example 40: The device of example 39, wherein the manifold block includes a block fluid intake port, a block fluid intake pathway, and a block intake connector port that aligns with communicates with the fluid intake port or the second fluid intake port, whereby fluid entering the block fluid intake port passes into the fluid intake port or the second fluid intake port and into the manifold.

Example 41: The device of example 39 or 40, wherein the manifold block includes a block fluid exit port, a block fluid exit pathway, and a block exit connector port that aligns with and communicates with the fluid exit port or the second fluid exit port, whereby fluid exiting the manifold passes through the fluid exit pathway and out of the manifold block.

Example 42: The device of any of examples 39-41, wherein the manifold block further includes a keyway that aligns and mates with a keyway on the manifold to properly align the manifold block and the manifold.

Example 43: The device of any of examples 39-42, wherein the manifold block further includes one or more block sensors in communication with the fluid passing through the manifold block.

Example 44: The device of example 43, wherein the one or more block sensors are selected to measure one or more parameters of the group consisting of: temperature, viscosity, pressure, density, dielectric constant, water content, flow rate, consumption rate, total volume, total acid number (TAN), total base number (TBN), oxidation numbers, nitration levels, oil SAE grade, amount of wear particles, and contamination particles.

Example 45: The device of example 43 or 44, wherein the one or more block sensors are configured to communicate with the PCBA through a wired or wireless connection.

Example 46: The device of any of examples 39-45, wherein the manifold block is supported by a support bracket.

Example 47: The device of any of examples 1-46 that is mounted on a stationary machine, a moving machine, or a moveable machine.

Example 48: The device of any of examples 4-47 that includes a spacer vent passage that extends from the spacer cavity to outside of the device, whereby the spacer vent passage is configured to equalize the pressure of the spacer cavity to the atmospheric pressure.

Example 49: The device of example 48, wherein the spacer vent passage passes partially through the manifold.

Example 50: The device of example 48 or 49, wherein the spacer vent passage further comprises a tube positioned in the spacer cavity.

Example 51: The device of any of examples 48-50, wherein the spacer vent passage includes a moisture-proof barrier configured to help prevent moisture from entering the spacer cavity.

Example 52: The device of example 51, wherein the moisture-proof barrier is Gortex® fabric.

Example 53: The device of any of examples 28-52, wherein the manifold further comprises a sample bottle mounting structure.

Example 54: The device of example 53, wherein the sample bottle mounting structure comprises threads.

Example 55: The device of example 54, wherein the sample bottle mounting structure further comprises a groove beneath the threads and an o-ring in the groove, wherein the o-ring has a thickness sufficient to extend outward past the groove.

Example 56: The device of example 55 that further includes a sample bottle connected to the sample bottle mounting structure, wherein the sample bottle has a top with an opening and bottle threads on an exterior surface of the top, and the bottle threads are received in the threads of the sample bottle mounting structure.

Example 57: The device of any of examples 28-56 that further includes a sample bottle venting passage configured to vent air from the sample bottle as the sample bottle receives a liquid sample.

Example 58: The device of example 57, wherein the sample bottle venting passage extends from the opening in the sample bottle, through the sample bottle mounting structure, and to outside of the device.

Example 59: The device of any of examples 53-58, wherein the sample bottle mounting structure is positioned in the manifold.

Example 60: The device of any of examples 57-59, wherein the sample bottle venting passage includes a moisture proof barrier configured to help prevent moisture from outside of the device from entering the sample bottle.

Example 61: The device of any of examples 53-60, wherein the sample bottle mounting structure further includes a protective container mounting structure.

Example 62: The device of example 61, wherein the protective container mounting structure is two outwardly-extending posts or fasteners.

Example 63: The device of example 61 or 62 that further includes a protective container positioned on the protective container mounting structure and over the sample bottle, whereby the protective container is configured to help protect the sample bottle.

Example 64: The device of example 63, wherein the protective container has a top that includes an opening, and two slots in the top that are configured to receive and be retained by the protective container mounting structure.

Example 65: The device of example 63 or 64, wherein the protective container is comprised of aluminum.

Example 66: The device of any of examples 63-65, wherein the protective container includes a transparent panel through which the sample bottle can be seen.

Example 67: The device of any of examples 33-66 that further includes a valve structure positioned at least partially in the manifold and in communication with the fluid pathway.

Example 68: The device of example 67, wherein the valve structure comprises a valve moveable from a first, closed position to a second, open position in which fluid can pass from the manifold into the sample bottle.

Example 69: The device of example 68, wherein the valve structure further comprises a solenoid.

Example 70: The device of any of examples 67-69, wherein the valve structure is positioned partially in the cavity of the spacer.

Example 71: The device of any of examples 67-70, wherein the valve structure is in communication with the PCBA and moves to its second, open position in response to a signal from the PCBA.

Example 72: The device of example 71, wherein the valve structure moves to its second, open position for a period of time determined by the PCBA and based upon (a) the type of fluid being sampled, (b) the sample size desired, (c) the temperature of the fluid, and (d) the pressure of the fluid.

Example 73: The device of any of examples 1-72 that is connected to a fluid bypass line on the machine, wherein the fluid bypass line has a first end connected to a main fluid line and through which fluid enters the fluid bypass line, and the bypass line has a second end connected to the main fluid line and by which fluid from the bypass line re-enters the main fluid line.

The present invention has been described above with reference to a number of exemplary embodiments and examples. The particular embodiments shown and described herein are illustrative of the exemplary embodiments, and are not intended to limit the scope of the invention. Changes and modifications may be made to the embodiments described herein without departing from the scope of the present invention. These and other changes or modifications are intended to be included within the scope of the claimed invention and the legal equivalents thereof.

What is claimed is:

1. A device mounted to a machine, the device being configured to monitor one or more fluid parameters of the machine, wherein the device comprises:
   (a) a printed circuit board assembly (PCBA);
   (b) a spacer that includes a power connector having a first end configured to be connected to an external power source, and a second end, and one or more sensor connectors, wherein the spacer has an inner cavity, a first end connected to the cover, and a second end connected to a manifold, wherein the second end has an inner, annular surface, and the inner, annular surface compresses an O-ring on the manifold to create a seal configured to keep particles and moisture out of the inner cavity of the spacer and out of an interior of the manifold, wherein the manifold further comprises a first fluid intake port, a second fluid intake port, a first fluid exit port, a second fluid exit port, a first fluid pathway between the first fluid intake port and the first fluid exit port, a second fluid pathway between the second fluid intake port and the second fluid exit port and connected to the first fluid pathway, and a manifold block comprising a block fluid exit port, a block fluid exit pathway, and a block exit connector port that aligns with and communicates with the first fluid exit port, whereby fluid exiting the manifold passes through the first fluid pathway and out of the manifold block;
   (c) a wire having a first end connected to the second end of the power connector and a second end connected to the PCBA; and
   (d) one or more sensors, wherein each of the one or more sensors is connected to one of the one or more sensor connectors and each of the one or more sensor connectors that is connected to one of the one or more sensors is also connected to the PCBA by a wired connection.

2. The device of claim 1, wherein the spacer has a top and a bottom and a cover attached to the top of the spacer.

3. The device of claim 1, wherein at least one of the one or more sensors is remote to the device.

4. The device of claim 1, wherein at least one of the one or more sensors is located on or in the device.

5. The device of claim 1, wherein the spacer further comprises an external antenna mount.

6. The device of claim 5 that further comprises an antenna mounted to the external antenna mount, wherein the antenna is in wired or wireless communication with the PCBA.

7. The device of claim 1, wherein the one or more sensors measure one or more of machine vibration, revolutions per minute (RPM), and torque.

8. The device of claim 1, wherein the one or more sensors comprise one or more of (a) an optical sensor, and (b) an internet-of-things sensor.

9. The device of claim 1, wherein the manifold further comprises a fluid temperature sensor located at one or more of the first fluid intake port, the first fluid pathway, and the first fluid exit port.

10. The device of claim 1, wherein the manifold further comprises a fluid pressure sensor located at one or more of the first fluid intake port, the first fluid pathway, and the first fluid exit port.

11. The device of claim 1, wherein two of the first fluid intake port, first fluid exit port, second fluid intake port, and second fluid exit port are plugged.

12. The device of claim 1, wherein the manifold block further comprises a block fluid exit port, a block fluid exit pathway, and a block exit connector port that aligns with and communicates with the fluid exit port or the second fluid exit port, whereby fluid exiting the manifold passes through the first fluid exit pathway and out of the manifold block.

13. The device of claim 1, wherein the manifold block further includes one or more block sensors in communication with the fluid passing through the manifold block and the one or more block sensors are configured to communicate with the PCBA through a wired or wireless connection.

14. The device of claim 1, that further includes a valve in the first fluid pathway, wherein the valve is movable between a first, closed position in which fluid cannot pass out of the manifold, and a second, open position in which fluid can pass out of the manifold.

15. The device of claim 14, wherein the manifold further comprises a sample bottle mounting structure configured to retain a sample bottle that receives the fluid that passes out of the manifold.

\* \* \* \* \*